(12) United States Patent
Zhou et al.

(10) Patent No.: US 7,687,432 B2
(45) Date of Patent: Mar. 30, 2010

(54) MESH-ADJUSTABLE MOLECULAR SIEVE

(75) Inventors: Hong-Cai Zhou, Oxford, OH (US);
Shengqian Ma, Oxford, OH (US)

(73) Assignee: Miami University, Oxford, OH (US)

( * ) Notice: Subject to any disclaimer, the term of this patent is extended or adjusted under 35 U.S.C. 154(b) by 400 days.

(21) Appl. No.: 11/738,730

(22) Filed: Apr. 23, 2007

(65) Prior Publication Data
US 2008/0184883 A1 Aug. 7, 2008

Related U.S. Application Data

(60) Provisional application No. 60/899,115, filed on Feb. 2, 2007.

(51) Int. Cl.
*B01D 53/02* (2006.01)
*B01J 20/22* (2006.01)
(52) U.S. Cl. .......................... 502/401; 556/1
(58) Field of Classification Search ............... 96/108; 95/90, 902; 556/1, 27, 170; 502/401, 526
See application file for complete search history.

(56) References Cited

U.S. PATENT DOCUMENTS

| | | | |
|---|---|---|---|
| 6,930,193 | B2 | 8/2005 | Yaghi et al. |
| 2004/0225134 | A1 | 11/2004 | Yaghi et al. |
| 2006/0057057 | A1 | 3/2006 | Muller et al. |
| 2006/0185388 | A1 | 8/2006 | Muller et al. |
| 2006/0210458 | A1 | 9/2006 | Mueller et al. |
| 2006/0252641 | A1 | 11/2006 | Yaghi et al. |

OTHER PUBLICATIONS

Long Pan et al; Porous Lanthanide-Organic Frameworks: Synthesis, Characterization, and Unprecedented Gas Adsorption Properties; JACS, Feb. 12, 2003, vol. 125, No. 10, pp. 3062-3067.
Long Pan et al; Zn(tbip) (H2tbip+5-tert-Butyl Isopthalic Acid): A Highly Stable Guest-Free Microporous Metal Organic Framework with Unique Gas Separation Capability; JACS, Mar. 14, 2006, vol. 128, No. 13, pp. 4180-4181.
Jasra et al; Separation of Gases by Pressure Swing Adsorption; Separation Science and Technology; 1991; vol. 26; pp. 885-930.
Ma, Shengqian et al.; A Mesh-Adjustable Molecular Sieve for General Use in Gas Separation; Angewandte Chemie, International Edition, journal; 2007; pp. 2458-2462; vol. 46.

(Continued)

*Primary Examiner*—Frank M Lawrence
(74) *Attorney, Agent, or Firm*—Jason H. Foster; Kremblas, Foster, Phillips & Pollick

(57) ABSTRACT

A metal-organic framework-based mesh-adjustable molecular sieve (MAMS) exhibiting a temperature-dependent mesh size. The MAMS comprises a plurality of metal clusters bound with a plurality of amphiphilic ligands, each ligand comprising a hydrophobic moiety and a functionalized hydrophilic moiety, and wherein the metal clusters and amphiphilic ligand functionalized hydrophilic moieties form a metal cluster layer, the metal cluster layer forming at least one hydrophilic pore. On each side of the metal cluster layer, a plurality of associated amphiphilic ligand hydrophobic moieties cooperate with the metal cluster layer to form a tri-layer and a plurality of tri-layers are packed in a facing-spaced apart relationship to form at least one hydrophobic pore.

111 Claims, 23 Drawing Sheets

OTHER PUBLICATIONS

Yaghi, Omar et al; Reticular Synthesis and the Design of New Materials; Review Article; Jun. 12, 2003; pp. 705-715; vol. 423; Nature Publishing Group.

Daofeng Sun et al; Construction of Open Metal-Organic Frameworks Based on Predesigned Carboxylate Isomers: From Achiral to Chiral Nets; Chem.Eur,J. 2006; pp. 3768-3776; Wiley.

Daofeng Sun et al; Temperature-Dependent Supramoleculat Stereoisomerism in Porous Copper Coordination Networks . . . ; Chem Commun 2005; pp. 5447-5449.

Susumu Kitagawa et al; Coordination Polymers; Review; 2004; pp. 2334-2375; Angew.Chem. Int. Ed.

Susumu Kitagawa et al; Dynamic Porous Properties of Coordination Polymers Inspired by Hydrogen Bonds; Tutorial Review; 2005; pp. 109-119; Chem. Soc. Rev.

Daofeng Sun et al; An Interweaving MOF with High Hydrogen Uptake; J.Am.Chem. Soc. 2006; pp. 3896-3897.

Shengqian Ma et al; A Metal-Organic Framework with Entatic Metal Centers Exhibiting . . . ; J.Am.Chem.Soc. 2006; pp. 11734-11735.

Ma, Shengqian et al.; Preparation and Gas Adsorption Studies of Three Mesh-Adjustable Molecular Sieves with a Common Structure; J. Am. Chem. Soc. 2009, 131; pp. 6445-6451.

Daeho Ko et al; Optimization of a Pressure-Swing Adsorption Process Using Zeolite 13X for CO2 Sequestration; Ind. Eng. Chem. Res.; 42; 2003; 339-348.

Davis, Mark E.; Ordered Porous Materials for Emerging Applications; Nature; vol. 417; Jun. 20, 2002; 813-821.

Shivaji Sircar et al; Gas Separation by Zeolites; No. 22; p. 063.

Cheetham et al; Open-Framework Inorganic Materials; Angew. Chem. Int. Ed. 1999; 38; 3268-3292.

Kuznicki et al; A Titanosilicate Molecular Sieve with Adjustable Pores for Size-Selective Adsorption of Molecules; Nature; vol. 412; Aug. 16, 2001; 720-724.

Kazuhiro Uemura et al; Flexible Microporous Coordination Polymers; Journal of Solid State Chemistry; 178; 2005; 2420-2429.

Ockwig et al; Reticular Chemistry: Occurrence and Taxonomy of Nets and Grammar for the Design of Frameworks; Acc. Chem. Res.; 38; 2005; 176-182.

Stuart R. Batten; Glorious Uncertainty-Challenges for Network Design; Journal of Solid State Chemistry; 178; 2005; 2475-2479.

Jung Soo Seo et al; A Homochiral Metal-Organic Porous Material for Enantioselective Separation and Catalysis; Nature; vol. 404; Apr. 27, 2000; 982-986.

Ru-Qiang Zou et al; Preparation, Adsorption Properties, and Catalytic Activity of 3D Porous Metal-Organic Frameworks Composed of Cubic Building Blocks and Alkali-Metal Ions; Angew. Chem. Int. Ed.; 45; 2006; 2542-2546.

Danil N. Dybtsev et al; A Homochiral Metal-Organic Material with Permanent Porosity, Enantioselective Sorption Properties, and Catalytic Activity; Angew. Chem. Int. Ed.; 45; 2006; 916-920.

Ryotaro Matsuda et al; Highly Controlled Acetylene Accommodation in a Metal-Organic Microporous Material; Nature; vol. 436; Jul. 14, 2005; 238-241.

Mircea Dinca et al; Strong H2 Binding and Selective Gas Adsorption within the Microporous Coordination Solid Mg3 (O2C-C10H6-CO2)3; J. Am. Chem. Soc.; 127; 2005; 9376-9377.

Danil N. Dybtsev et al; Microporous Manganese Formate: A Simple Metal-Organic Porous Material with High Framework Stability and Highly Selective Gas Sorption Properties; J. Am. Chem. Soc.; 126; 2004; 32-33.

Banglin Chen et al; A Microporous Metal-Organic Framework for Gas-Chromatographic Separation of Alkanes; Angew. Chem. Int. Ed.; 45; 2006; 1390-1393.

Long Pan et al; Separation of Hydrocarbons with a Microporous Metal-Organic Framework; Angew. Chem. Int. Ed.; 45; 2006; 616-619.

Banglin Chen et al; Rationally Designed Micropores within a Metal-Organic Framework for Selective Sorption of Gas Molecules; Inorganic Chemistry; vol. 46, No. 4; 2007; 1233-1236.

Rowsell et al; Strategies for Hydrogen Storage in Metal-Organic Frameworks; Angew. Chem. Int. Ed.; 44; 2005; 4670-4679.

Banglin Chen et al; High H2 Adsorption in a Microporous Metal-Organic Framework with Open Metal Sites; Angew. Chem. Int. Ed.; 44; 2005; 4745-4749.

Rowsell et al; Effects of Functionalization, Catenation, and Variation of the Metal Oxide and Organic Linking Units on the Low-Pressure Hydrogen Adsorption Properties of Metal-Organic Frameworks; J. Am. Chem. Soc.; 128; 2006; 1304-1315.

Mohamed Eddaoudi et al; Systematic Design of Pore Size and Functionality in Isoreticular MOFs and Their Application in Methane Storage; Science 295; 2002; 469.

Millward et al; Metal-Organic Frameworks with Exceptionally High Capacity for Storage of Carbon Dioxide at Room Temperature; J. Am. Chem. Soc.; 126; 2005; 17998-17999.

P. Sozzani et al; Methane and Carbon Dioxide Storage in a Porous van der Waals Crystal; Angew. Chem. Int. Ed.; 44; 2005; 1816-1820.

Atwood et al; Guest Transport in a Nonporous Organic Soilid via Dynamic van der Waals Cooperativity; Science 298; 1000; 2002.

Qisheng Huo et al; Generalized Synthesis of Periodic Surfactant/Inorganic Composite Materials; Nature; vol. 368; Mar. 24, 1994; 317-321.

Yanxiong Ke et al; Synthesis and Structure of Cuboctahedral and Anticuboctahedral Cages Containing 12 Quadruply Bonded Dimolybdenum Units; Inorganic Chemistry; vol. 44, No. 12; 2005; 4154-4156.

A. Bondi; van der Waals Volumes and Radii; The Journal of Physical Chemistry; vol. 68, No. 3; Mar. 16, 1964; 441-451.

Beck; Adsorption by Dehydrated Zeolite Crystals; Table 8.14—Table of Dimensions for Various Molecules (66); 636.

Omar M. Yaghi et al; Synthetic Strategies, Structure Patterns, and Emerging Properties in the Chemistry of Modular Porous Solids; Accounts of Chemical Research; vol. 31, No. 8; 1998; 474-484.

Moulton et al; From Molecules to Crystal Engineering: Supramolecular Isomerism and Polymorphism in Network Solids; Chem. Rev. 2001; 101; 1629-1658.

Banu Kesanli et al; Highly Interpenetrated Metal-Organic Frameworks for Hydrogen Storage; Angew. Chem. Int. Ed.; 44; 2005; 72-75.

Mircea Dinca et al; Hydrogen Storage in a Microporous Metal-Organic Framework with Exposed Mn2+ Coordination Sites; J. Am. Chem. Soc.; 128; 2006; 16876-16883.

Banglin Chen et al; Hydrogen Adsorption in an Interpenetrated Dynamic Metal-Organic Framework; Inorganic Chemistry; vol. 45; No. 15; 2006; 5718-5720.

Xi-Sen Wang et al; A Mesoporous Metal-Organic Framework with Permanent Porosity; J. Am. Chem. Soc.; 128; 2006; 16474-16475.

Shengqian Ma et al; Framework-Catenation Isomerism in Metal-Organic Frameworks and its Impact on Hydrogen Uptake; J. Am. Chem. Soc.; 129; 2007; 1858-1859.

Shengqian Ma et al; Metal-Organic Framework from an Anthracene Derivative Containing Nanoscopic Cages Exhibiting High Methane Uptake; J. Am. Chem. Soc.; 130; 2008; 1012-1016.

Aiguo Hu et al; Chiral Porous Hybrid Solids for Practical Heterogeneous Asymmetric Hydrogenation of Aromatic Ketones; J. Am. Chem. Soc.; 125; 2003; 11490-11491.

Halder et al; Guest-Dependent Spin Crossover in a Nanoporous Molecular Framework Material; Science 298; 1762; 2002.

Janiak, Christopher; Engineering Coordination Polymers Towards Applications; The Royal Society of Chemistry; 2003; 2781-2804.

Yan-Zhen Zheng et al; Assembling Magnetic Nanowires into Networks: A Layered COII Carboxylate Coordination Polymer Exhibiting Single-Chain-Magnet Behavior; Angew. Chem. Int. Ed.; 45; 2006; 6310-6314.

Chengtao Yu et al; Magnetic Properties of a Noninterpenetrating Chiral Porous Cobalt Metal-Organic Framework; Journal of Applied Physics; 101; 2007; 09E108-1-09E108-3.

Humphrey et al; Porous Cobalt(II)-Organic Frameworks with Corrugated Walls: Structurally Robust Gas-Sorption Materials; Angew. Chem. Int. Ed.; 46; 2007; 272-275.

Banglin Chen et al; A Microporous Metal-Organic Framework for Gas-Chromatographic Separation of Alkanes; Angew. Chem. Int. Ed.; 45; 2006; 1390-1393.

Banglin Chen et al; Rationally Designed Micropores within a Metal-Organic Framework for Selective Sorption of Gas Molecules; Inorganic Chemistry; vol. 46; No. 4; 2007; 1233-1236.

Shengqian Ma et al; Metal-Organic Framework Based on a Trinickel Secondary Building Unit Exhibiting Gas-Sorption Hysteresis; Inorganic Chemistry; vol. 46; No. 9; 2007; 3432-3434.

Shengqian Ma et al; Ultramicroporous Metal-Organic Framework Based on 9, 10-Anthracenedicarboxylate for Selective Gas Adsorption; Inorganic Chemistry; vol. 46; No. 21; 2006; 8499-8501.

Banglin Chen et al; A Triply Interpenetrated Microporous Metal-Organic Framework for Selective Sorption of Gas Molecules; Inorganic Chemistry; vol. 46; No. 21; 2007; 8490-8492.

Kazuhiro Uemura et al; Flexible Microporous Coordination Polymers; Journal of Solid State Chemistry; 178; 2005; 2420-2429.

D. Bradshaw et al; Design, Chirality, and Flexibility in Nanoporous Molecule-Based Materials; Acc. Chem. Res.; 38; 2005; 273-282.

Shengqian Ma et al; A Mesh-Adjustable Molecular Sieve for General Use in Gas Separation; Angew. Chem. Int. Ed.; 46; 2007; 2458-2462.

A. L. Spek; Single-Crystal Structure Validation with the Program PLATON; J. Appl. Cryst.; 36; 2003; 7-13.

R. E. Rondeau; Slush baths; Journal of Chemical and Engineering Data; 1965; 124.

Phipps et al; General Purpose Low Temperature Dry-Ice Baths; Journal of Chemical Education; 664.

Danil N. Dybtsev et al; Rigid and Flexible: A Highly Porous Metal-Organic Framework with Unusual Guest-Dependent Dynamic Behavior; Angew. Chem. Int. Ed.; 43; 2004; 5033-5036.

Hyungphil Chun et al; Synthesis, X-ray Crystal Structures, and Gas Sorption Properties of Pillared Square Grid Nets Based on Paddle-Wheel Motifs: Implications for Hydrogen Storage in Porous Materials; Chem. Eur. J.; 11; 2005; 3521-3529.

Bao-Qing Ma et al; Microporous Pillared Paddle-Wheel Frameworks Based on Mixed-Ligand Coordination of Zinc Ions; Inorganic Chemistry; vol. 44; No. 14; 2005; 4912-4914.

Eun-Young Choi et al; Benzene-Templated Hydrothermal Synthesis of Metal-Organic Frameworks with Selective Sorption Properties; Chem. Eur. J.; 10; 2004; 5535-5540.

Banglin Chen et al; Selective Gas Sorption within a Dynamic Metal-Organic Framework; Inorganic Chemistry; vol. 46; No. 21; 2007; 8705-8709.

Rosseinsky; Recent Developments in Metal-Organic Framework Chemistry: Design, Discovery, Permanent Porosity and Flexibility; Microporous and Mesoporous Materials; 73; 2004; 15-30.

Rowsell; Metal-Organic Frameworks: A New Class of Porous Materials; Microporous and Mesoporous Materials; 73; 2004; 3-14.

○ Ni
● O
◐ $\mu_3$-OH
● $H_2O$
◎ C

4'-tert-butyl-biphenyl-3,5-dicarboxylate
BBPDC

4'-methyl-biphenyl-3,5-dicarboxylate
MBPDC 5-isopropyl-1,3-benzene-dicarboxylate
PBDC 4'-isopropyl-biphenyl-3,5-dicarboxylate
PBPDC 4'-trifluoromethyl-biphenyl-3,5-dicarboxylate
TFMBPDC 3',5'-di-tert-butyl-biphenyl-3,5-dicarboxylate
DBBPDC 3',5'-bis-trifluormethyl-biphenyl-3,5-dicarboxylate
BTFMBPDC 3',5'-diisopropyl-biphenyl-3,5-dicarboxylate
DPBPDC 3,5-di-tert-butyl-benzoate
DBB 3,5-di-tert-butyl-4-hydroxy-benzoate
DBHB 4-tert-butyl-benzoate
TBB 4-isopropyl-benzoate
IPB 5-tert-butyl-1,3-benzenediimidazolate
BBDI 5-tert-butyl-1,3-benzenedi(3'-pyridine)
3'-BBDP 5-tert-butyl-1,3-benzenedi(4'-pyridine)
4'-BBDP 5-tert-butyl-1,3-benzenedi(3'H-3'pyrizole)
3'-BBDPz 5-tert-butyl-1,3-benzenedi(3'H-4'pyrizole)
4'-BBDPz 5-tert-butyl-1,3-benzene dicarboxylate
BBDC 5-butoxy-1,3-benzenedicarboxylate
BOBDC 5-butylsulfonyl-1,3-benzenedicarboxylate
BSBDC 5-tert-butyl-5,5-benzeneditetrazolate
BBDT

MESH-ADJUSTABLE MOLECULAR SIEVE

CROSS-REFERENCES TO RELATED APPLICATIONS

This application claims the benefit of U.S. Provisional Application No. 60/899,115 filed Feb. 2, 2007.

STATEMENT REGARDING FEDERALLY-SPONSORED RESEARCH AND DEVELOPMENT

This invention was made in the course of research partially supported by a grant from the National Science Foundation (CHE-0449634). The government has certain rights in this invention.

REFERENCE TO AN APPENDIX (Not Applicable)

BACKGROUND OF THE INVENTION

1. Field of the Invention

This invention relates generally to metal-organic framework-based molecular sieves for selective gas adsorption and particularly to such sieves which provide dynamic mesh sizes which are continuously adjustable.

2. Description of the Related Art

Gas separation is an important operation in many industries and conventional processes include distillation, absorption, and molecular sieves. However, using such processes to separate, for example, mixtures comprising chemical pairs of similarly-sized molecules or those with similar boiling points such as ethylene and propylene, methane and ethylene, nitrogen and methane, nitrogen and oxygen, hydrogen and carbon monoxide, and hydrogen and nitrogen can be difficult.

Recently, metal-organic frameworks (MOFs) have been utilized to produce porous materials suitable as molecular sieves for adsorbing specific molecular species. Such frameworks, which comprise metal clusters linked together in a reticular structure with linking ligands, can provide predetermined pore size and functionality. However, when the size disparity of the gas pairs to be separated is small, a molecular sieve with the optimum mesh size is not always readily available and a mismatch inevitably leads to an inefficient operation. Furthermore, the mesh size of even MOFs is fixed upon activation. Therefore, the need exists for a mesh-adjustable molecular sieve (MAMS) capable of dynamically providing a continuum of mesh sizes. Particularly, the need exists for a MAMS having a continuum of mesh sizes in the range of most commercially-important gas separations.

BRIEF SUMMARY OF THE INVENTION

The invention is a metal-organic framework-based (MOF) mesh-adjustable molecular sieve (MAMS). MAMSs exhibit permanent porosity, characterized by strong bonds, and exhibit temperature-induced dynamically-flexible molecular gating effects, requiring weak interactions, to enable selective adsorption of molecules of interest. A MAMS comprises a layered, generally graphitic, structure wherein the atoms of each layer are connected coordinatively but the layers are held together with weak interactions. Such a structure is obtained by, first, employing an amphiphilic ligand comprising a hydrophobic end and a hydrophilic end, but with the hydrophilic end functionalized with, for example, groups such as carboxylates. The ligand acts as one of two secondary building units (SBUs). The functional groups of the ligand bind metal ions/clusters (the second of the two SBUs) and the structure propagates into a generally two-dimensional sheet or layer. Two layers of ligands sandwich a metal ion/cluster layer to define three-dimensional tri-layers which pack through van der Waals interaction. The tri-layer, then, comprises a hydrophilic cluster layer sandwiched by two hydrophobic ligand layers. Essentially linear hydrophilic pores are created in the middle layer, and the packed tri-layers, with exposed hydrophobic exteriors, define hydrophobic pores. The hydrophobic pores are accessible through the hydrophobic/hydrophilic interface where the hydrophobic ends of adjacent ligands generally point toward each other. The MAMS exhibits a temperature-dependent mesh size which is substantially continuously and dynamically variable in a region of interest of between about 2.9 Å and about 5 Å.

DETAILED DESCRIPTION OF THE INVENTION

Figure 1A:
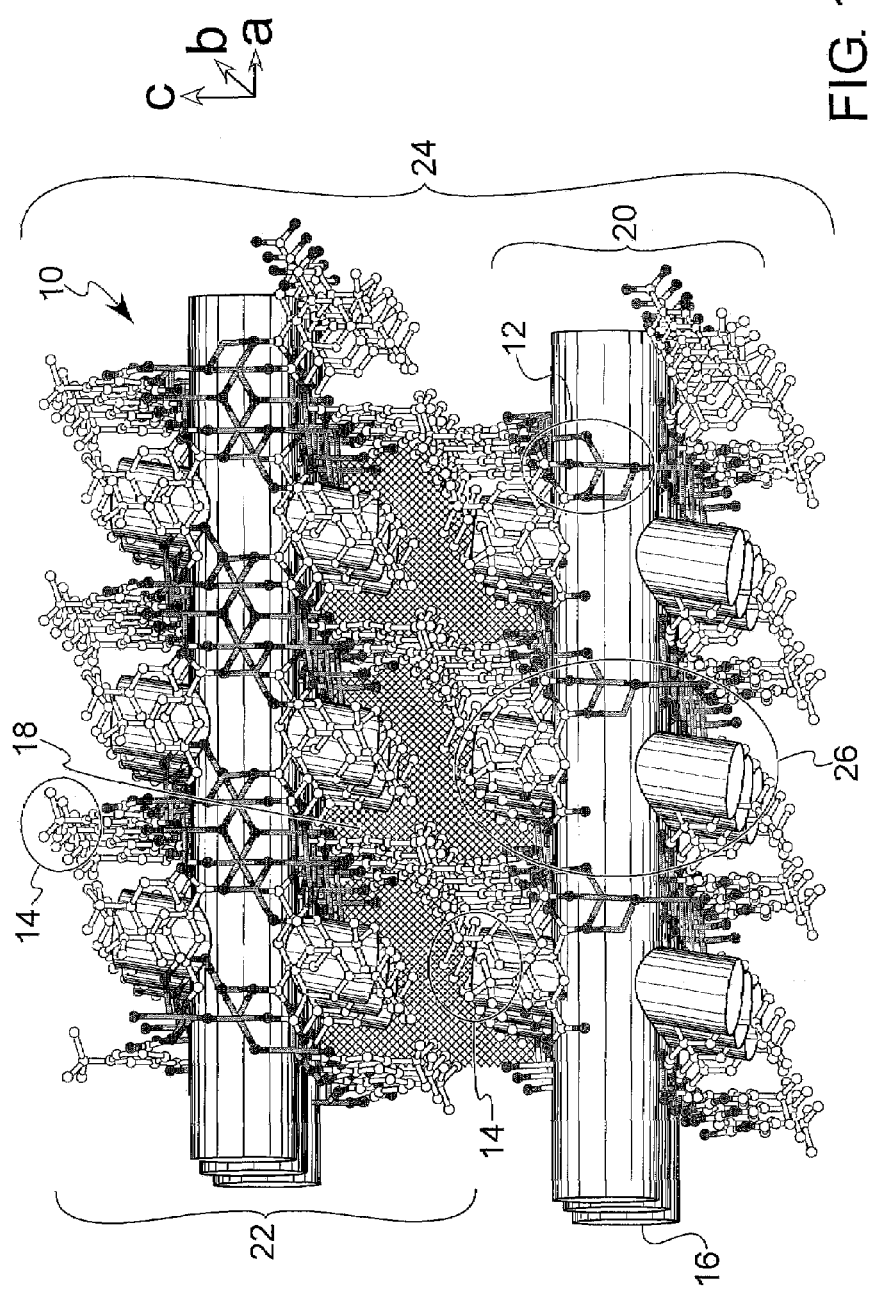
FIG. 1a is a conceptual three-dimensional graphical rendition of an exemplary MAMS illustrating the molecular structure and the defined pores.
Figure 1B:
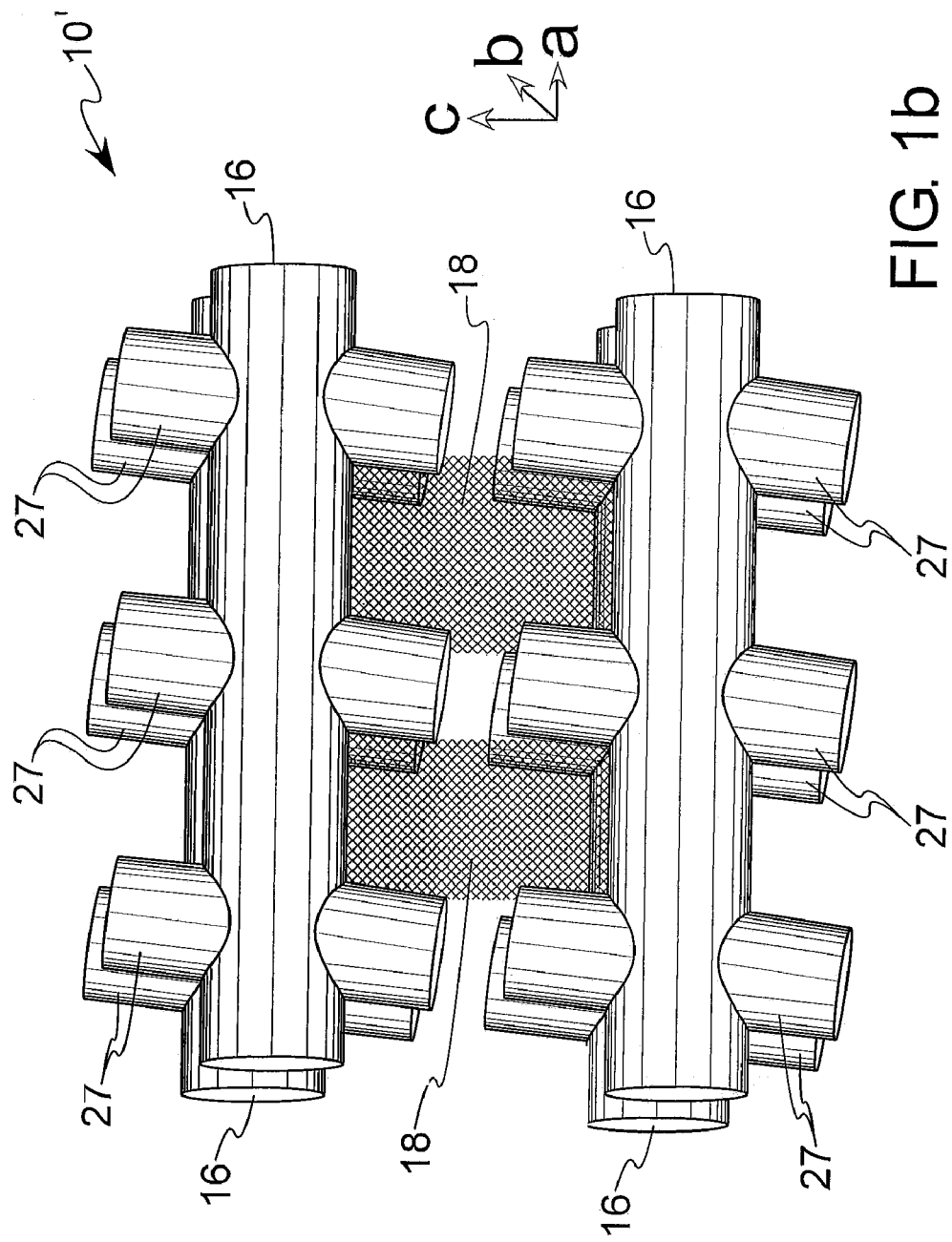
FIG. 1b is a simplified conceptual three-dimensional graphical rendition of an exemplary MAMS.
Figure 2A:
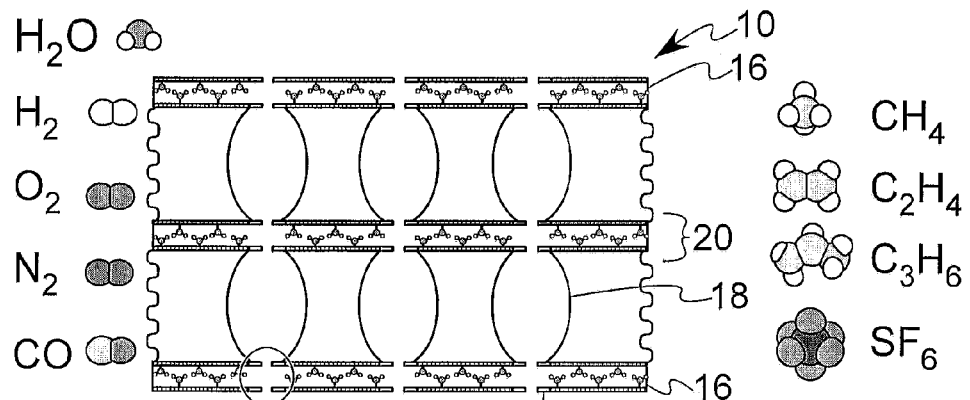
FIGS. 2a-2c are conceptual two-dimensional graphical renditions of an exemplary MAMS illustrating the defined pores, activation, and separable molecules.
Figure 2B:
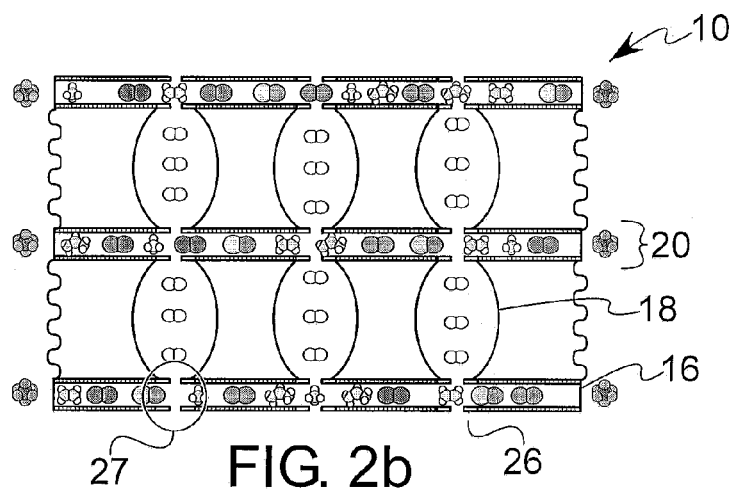
Figure 2C:
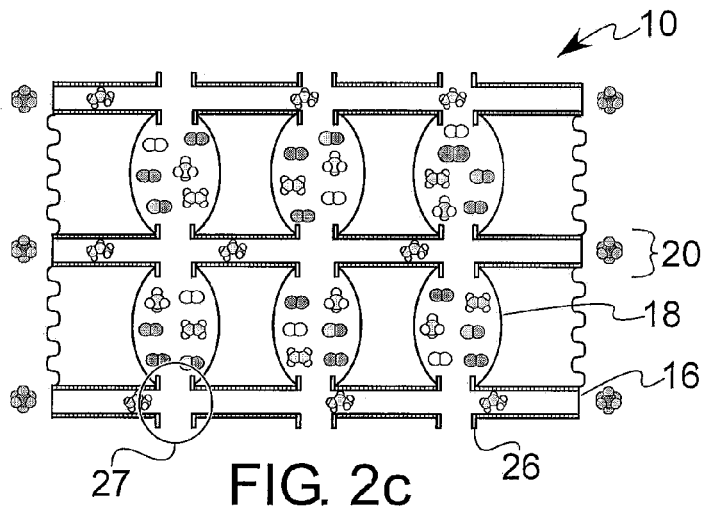
Figure 3A:
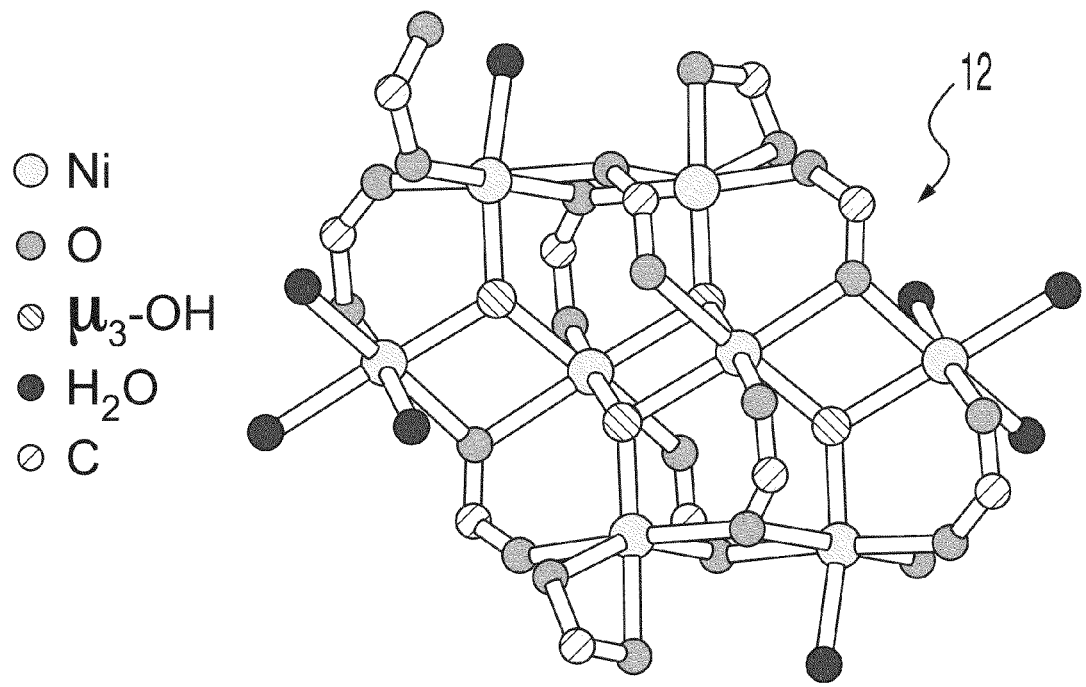
FIG. 3a is three-dimensional graphical rendition of an exemplary octa-nickel metal cluster prior to activation.
Figure 3B:
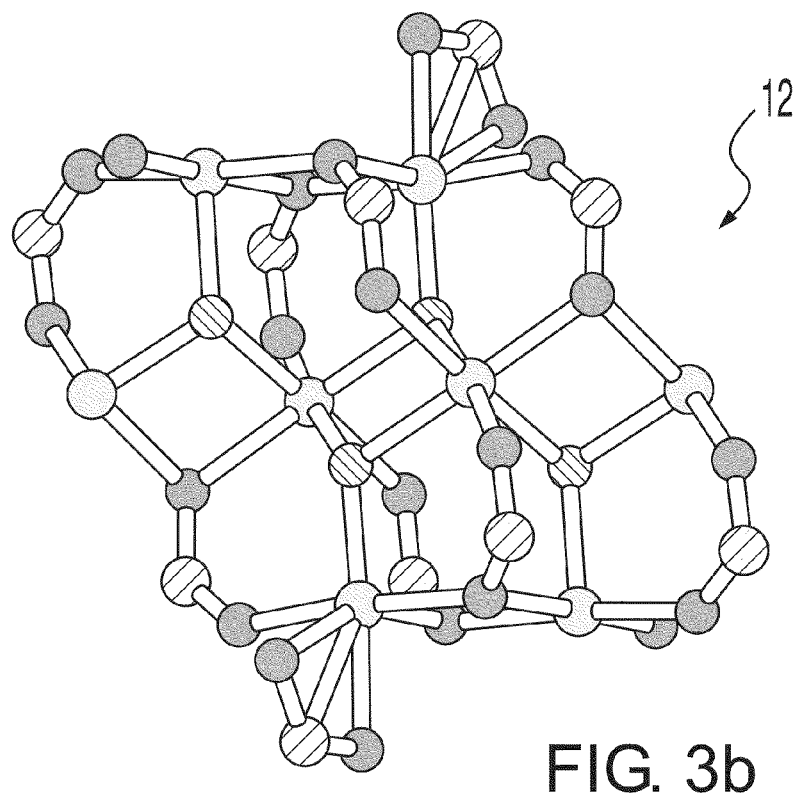
FIG. 3b is a three-dimensional graphical rendition of an exemplary octa-nickel metal cluster after activation.
Figure 3C:
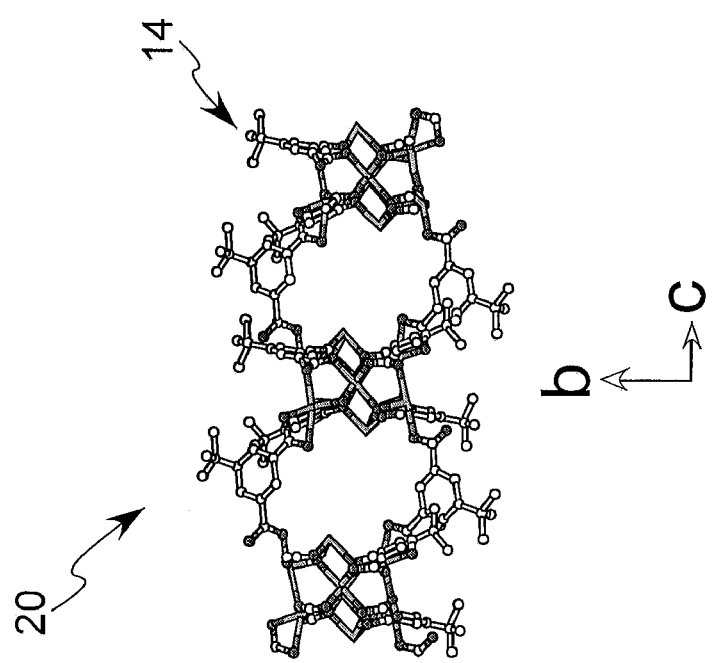
FIG. 3c is a three-dimensional graphical rendition of an exemplary metal cluster layer before and after activation.
Figure 3C:
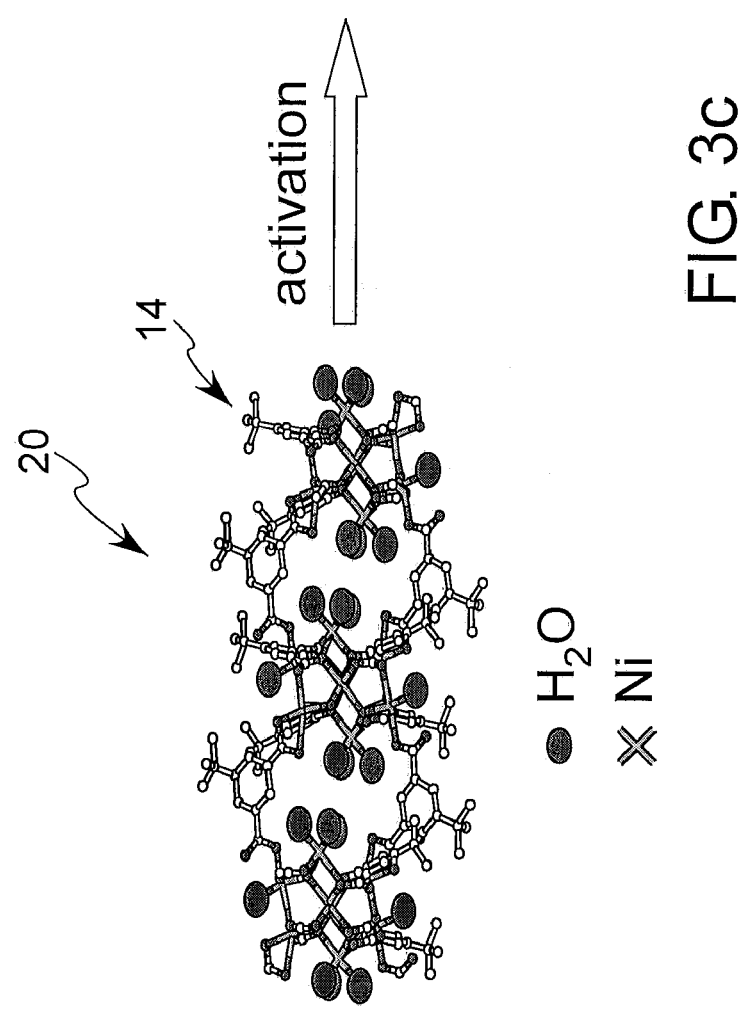
Figure 4B:
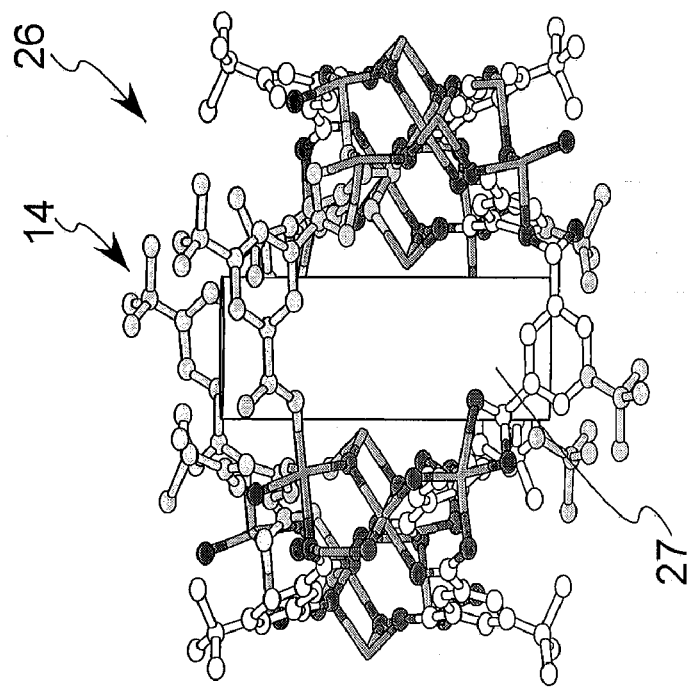
FIGS. 4a and 4b are conceptual three-dimensional graphical renditions of two views of a possible exemplary molecular gate-like structure.
Figure 4A:
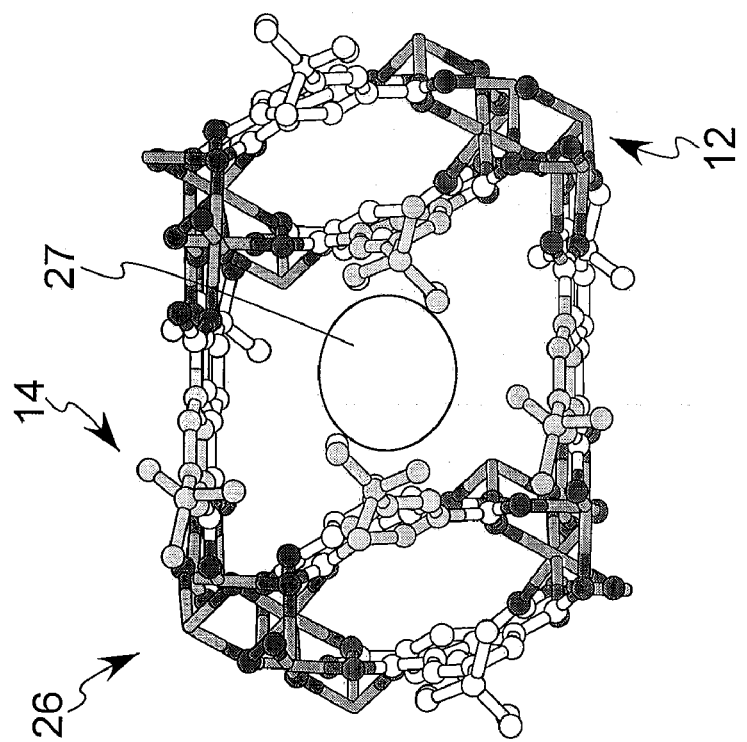
Figure 5:
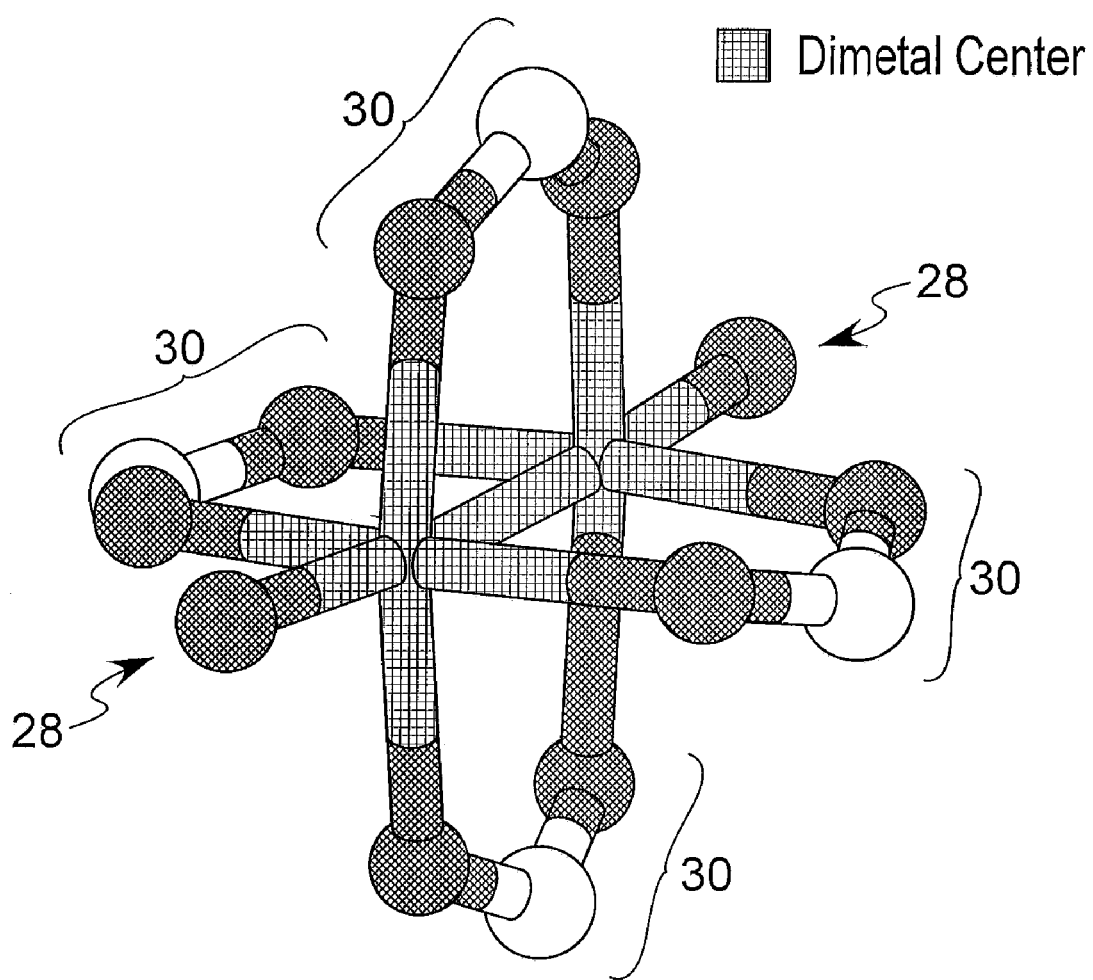
FIG. 5 is a three-dimensional graphical rendition of an exemplary bi-metal SBU.
Figure 9A:
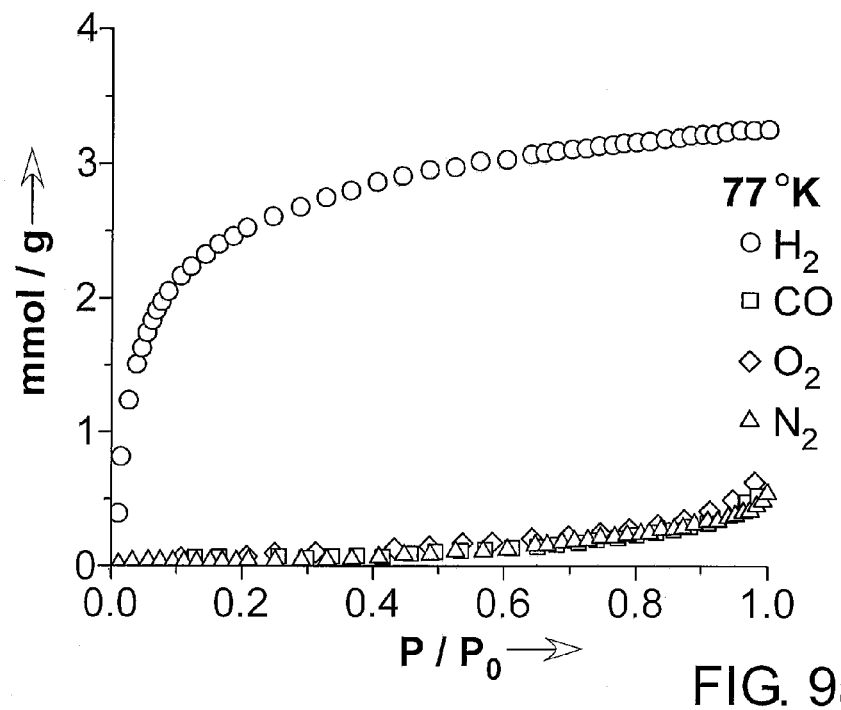
FIGS. 9a-9f illustrate gas adsorption isotherms for selected molecular species mixtures at selected temperatures for $Ni_8(\mu_3-OH)_4$(5-tert-butyl-1,3-benzenedicarboxylate)$_6$ (MAMS-1).

As shown in conceptual exemplary fashion in FIGS. 1*a*, 1*b*, and 2*a*-2*c*, the present invention relates to metal-organic framework-based (MOF) mesh-adjustable molecular sieves (MAMS) (e.g., 10, FIGS. 1*a* and 1*b* and FIGS. 2*a*-2*c*) suitable for selective gas adsorption and comprising metal clusters or metal ions (e.g., 12, FIGS. 1*a* and 3*a*-3*c*-5) cooperating with amphiphilic ligands (e.g., FIGS. 8*a*-8*e*), which ligands comprise a hydrophobic moiety (e.g., 14, FIGS. 1*a*, 4*a*, and 4*b*) and a functionalized hydrophilic moiety (e.g., FIGS. 8*a*-8*e*) wherein the metal clusters or metal ions 12 are coordinatively bound with functionalized hydrophilic moieties to form metal cluster layers 20, which each metal cluster layer 20 forms at least one hydrophilic pore 16, on each side of the metal cluster layer 20, associated amphiphilic ligand hydrophobic moieties 14 cooperate with the metal cluster layer 20 to form a tri-layer 22, and the tri-layers 22 are packed in a facing, spaced-apart relationship to form at least one hydrophobic pore 18 capable of adsorbing gas molecules of interest (e.g., FIGS. 2*a*-2*c*). In general, based upon the results and observations presented and discussed herein, while not wishing to be bound by any particular theory, it is believed a temperature-dependent gating effect arises from the positioning of the hydrophobic moieties 14 of the amphiphilic ligands. As shown in exemplary FIGS. 2*a*-2*c*, when the gates 26 are open the hydrophilic pores 16 and hydrophobic pores 18 are all connected, giving rise to a three-dimensional container with space continuity, which would account for the high uptake of selected molecular species (e.g., FIG. 9*a*). (See, also FIGS. 1*a*, 4*a*, and 4*b*.) It is likely that the molecular sieving effect comes, at least partially, from the hydrophobic moieties 14 of the amphiphilic ligands. (FIGS. 8*a*-8*e*.) For example, in view of the kinetic diameters of $H_2$ (2.89 Å), $O_2$ (3.46 Å), $N_2$ (3.64 Å), CO (3.76 Å), one may infer the gate opening 26, 27 for exemplary MAMS-1 (described in detail below) is about 3.0 Å to about 3.4 Å. (FIG. 9*a*.)

The metal is selected from the group consisting of transition metals, Al, Ge, and Ga and the amphiphilic ligand (e.g., FIGS. 8*a*-8*e*) is selected from the group consisting of:

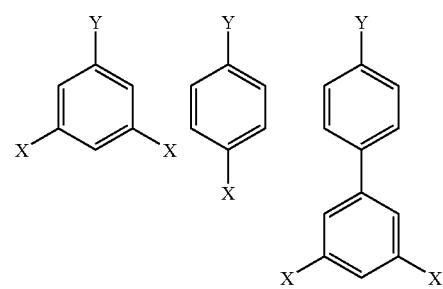

-continued

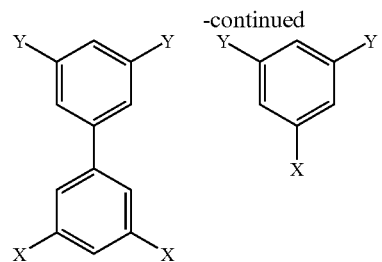

wherein X is at least one of carboxylate, cyano, and phosphate, sulfonate, imidazolate, pyridine, pyrazole, and tetrazolate and Y is at least one of tert-butyl, methyl, isopropyl, trifluoromethyl, butoxyl, and butylsulfonyl, alkyl, halogenated alkyl, alkenyl, alkynyl, and alkoxyl. MAMS 10 may be conceptualized as comprising secondary building units (SBU), the metal clusters forming one SBU 12 (e.g., $Ni_8(\mu_3\text{-}OH)_4$) (FIGS. 3*a* and 3*b*) and the ligands forming a second SBU (e.g., 5-tert-butyl-1,3-benzenedicarboxylate (BBDC)). In this MAMS, denoted MAMS-1, the eight octa-nickel atoms are divided into four pairs by a two-fold axis through the center of the cluster, a first Ni pair is bound to five carboxylate O atoms from four 5-BBDC ligands and one $\mu_3$-OH groups, a second Ni pair is bound to three carboxylate O atoms and three $\mu_3$-OH groups, a third Ni pair is bound to four carboxylate O atoms and one $\mu_3$-OH group, and a fourth Ni pair is bound to two carboxylate O atoms and one $\mu_3$-OH group. Thus, in MAMS-1, every octa-nickel cluster connects 12 BBDC ligands, and every BBDC ligand binds two octa-nickel cluster to comprise a tri-layer, with a hydrophilic cluster layer sandwiched by two hydrophobic GGDC layers (FIG. 1*a*). There are one-dimensional pores 16 along the a axis (FIG. 1*a*) in the middle layer, in which guest water solvates reside. (FIG. 2*a*.) The tri-layers, with their exposed hydrophobic exteriors 14, pack along the c axis through van der Waals forces (FIG. 1*a*), thus forming hydrophobic pores 18 between adjacent tri-layers 22. The metal cluster SBUs 12 are generally of the form $M_XA_Y$ wherein M is preferably a transition metal, Al, Ge, or Ga and A comprises oxo, hydroxyl, sulfur, and halogen. The ligand SBUs are shown generally above and in FIGS. 8*a*-8*e*. Other exemplary metal cluster SBUs include $Cu_2$, $Co_2$, $Mn_2$, and $Zn_2$. Other exemplary MAMS include $Cu_2(MBPDC)_2$, $Co_2(BBPDC)_2$, $Mn_2(BBPDC)_2$, $Zn_2(BBPDC)_2$, and $Cu_2(BBPDC)_2$, wherein BBDC is 5-tert-butyl-1,3-benzenedicarboxylate, MBPDC is 4'-methyl-biphenyl-3,5-dicarboxylate, and BBPDC is 4'-tert-butyl-biphenyl-3,5-dicarboxylate.

Figure 10:
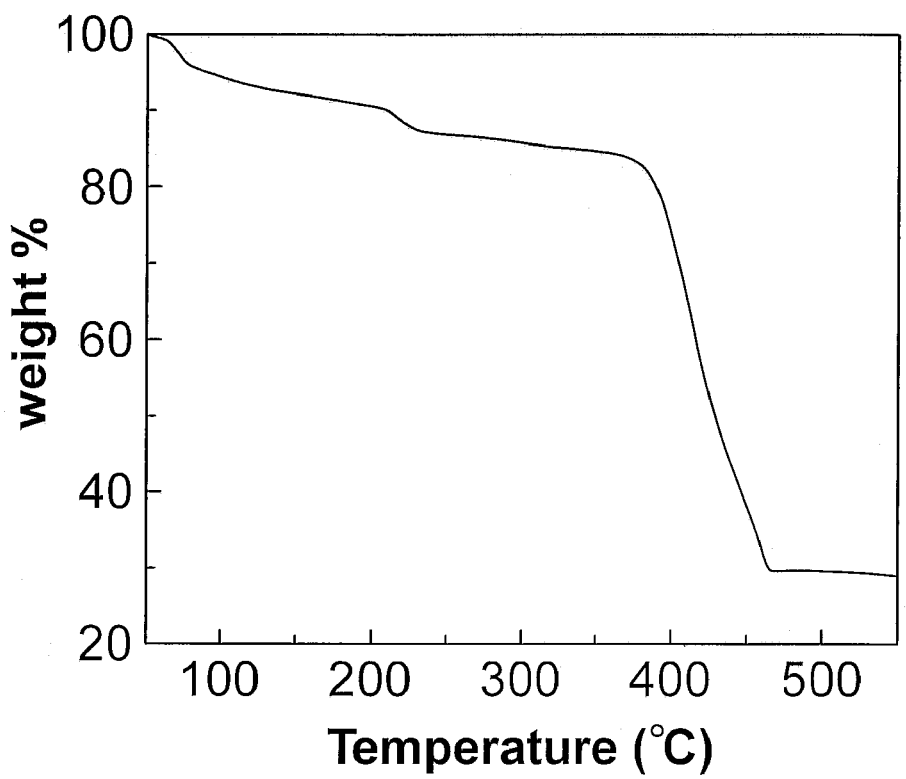
FIG. 10 illustrates a thermogravimetric analysis (TGA) of MAMS-1.

Freshly synthesized and isolated MAMSs 10, however, are not active for adsorption. (FIGS. 2*a*-2*c*, 3*a*, 3*b*, and 12-14.) As shown for MAMS-1 (10, FIGS. 1*a* and 1*b*) in FIGS. 12 and 13, for example, $H_2$ and CO are not adsorbed until MAMS-1 10 is activated at an elevated temperature. This phenomenon is further illustrated generically in FIGS. 2*a* and 2*b*. A thermogravimetric analysis of MAMS-1 10, for example, revealed a loss of eight guest water molecules from 50 deg. C. to 120 deg. C. and the release of eight bound aqua ligands per formula unit when heated to 250 deg. C. (FIG. 10.) For MAMS-1, the pre-activation formula is: $Ni_8(\mu_3\text{-}OH)_4(C_{12}H_{12}O_4)_6(H_2O)_8 \cdot 8H_2O$ and the activated formula is: $Ni_8(\mu_3\text{-}OH)_4(C_{12}H_{12}O_4)_6$, where $C_{12}H_{12}O_4$ is 5-tert-butyl-1,3-benzenedicarboxylate (BBDC).

The hydrophilic pores 16 alone appear to not be responsible for the gas uptake. In fact, they seem to account for a very minor part of the adsorption. As shown for MAMS-1 10, for example, in FIG. 9a, at 77 deg. K, only $H_2$ can enter the hydrophobic pores 18, showing significant uptake. At 77 deg. K, other molecules ($CO$, $O_2$, and $N_2$) cannot move beyond the hydrophilic pores 16 and the uptake of these gases is very low.

The hydrophilic pores 16, preferably exhibiting an atom-to-atom distance of about 8 Angstroms (Å) and an atom-to-atom distance of about 5 Å considering van der Waals radii, reach the structural limits the MAMS 10 and are in communication with the hydrophobic pores 18 via the molecular gates 26 and gateways 27 (FIGS. 1a, 2a-2c, 4a, and 4b). Again, while not wishing to be bound by any particular theory, it is believed molecular gates 26, formed by a pair of ligand groups (FIGS. 8a-8e) which are held in close proximity via van der Waals interaction, which is readily weakened by thermal vibration, preferably exhibit a continuously thermally-adjustable size in the single-digit Angstrom range, preferably between about 2.9 Å and about 5 Å. As will be appreciated by those skilled in the art, it is likely that the gate effect is not just the result of thermal vibration of the hydrophobic moiety alone as the other portions of the molecular structure, particularly the phenyl ring, for example, will also contribute somewhat. When the temperature is precisely controlled, any gate/gateway 26, 27 effect or mesh size within this range can be accurately attained. This molecular gate/gateway 26, 27 effect size range covers almost all commercially-important gas separations. For example, $H_2/N_2$, $H_2/CO$, $N_2/O_2$, $N_2/CH_4$, $CH_4/C_2H_4$ and $C_2H_4/C_3H_6$, wherein the molecules are separated from their respective pair. Exemplary kinetic diameters include $H_2$ (2.89 Å), $O_2$ (3.46 Å), $N_2$ (3.64 Å), $CO$ (3.76 Å), $CH_4$ (3.8 Å), $C_2H_4$, (3.8 Å), $C_3H_6$, (4.5 Å), and $SF_6$ (5.5 Å).

Figure 16:
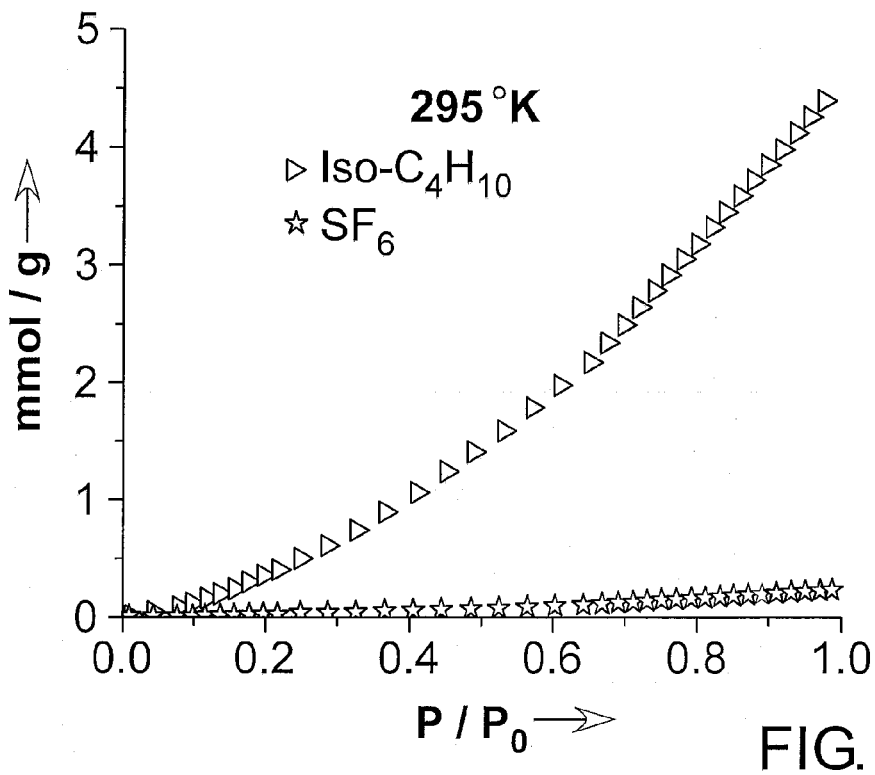
FIG. 16 illustrates iso-$C_4H_{10}$ and $SF_6$ adsorption isotherms at 295 deg. K for MAMS-1.

In operation, it is believed gas molecules enter the hydrophobic pores 18 through the hydrophilic pores 16 and gates 26 in the hydrophobic/hydrophilic interface. (FIGS. 1a, 1b, and 2a-2c.) It has been found, for example, that when the kinetic diameter of the gas molecule (e.g., $SF_6$ at 5.5 Å) exceeds the size of the hydrophilic pores 16 (5.0 Å considering van der Waals radii), no meaningful uptake was observed in an adsorption study. (FIGS. 2a-2c and 16.) The upper limit of the hydrophilic pore 16 is also consistent with an adsorption study on iso-$C_4H_{10}$ (5.0 Å) which entered MAMS-1 10 at room temperature (295 deg. K). (FIG. 16.)

Figure 20:
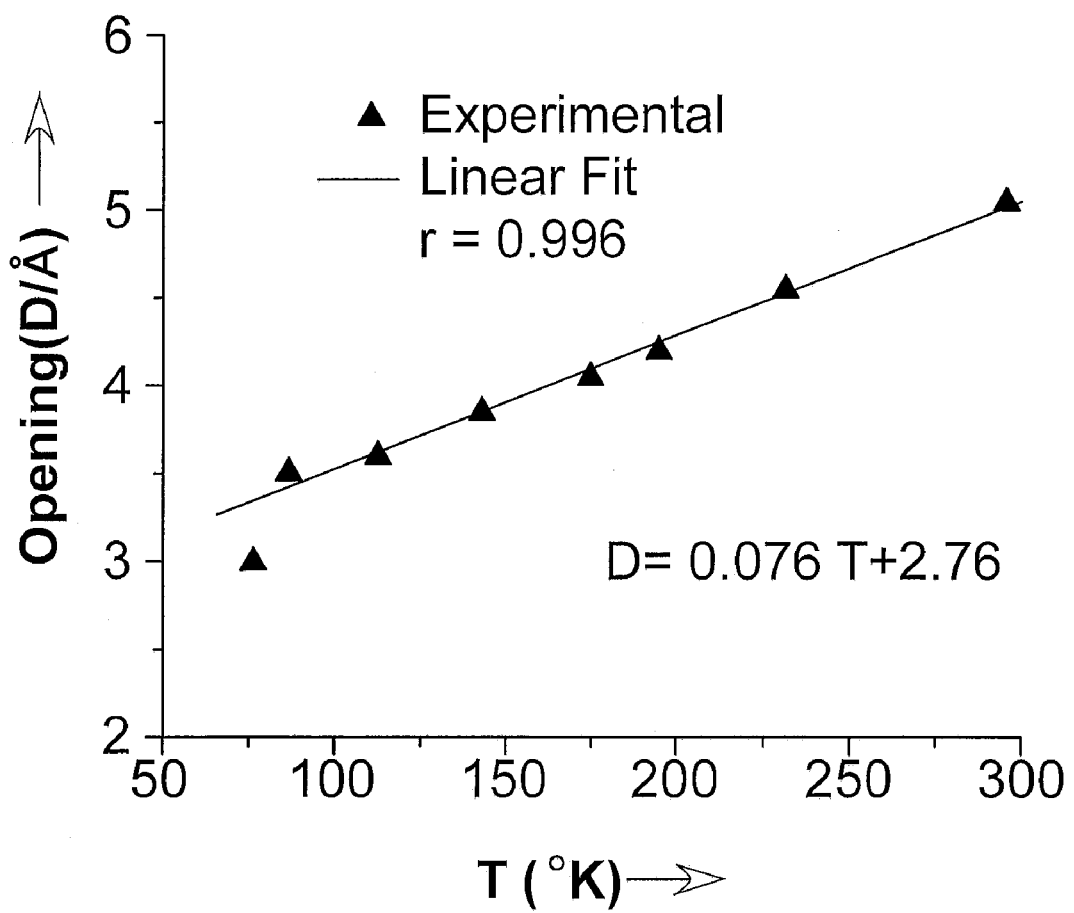
FIG. 20 illustrates the temperature-dependent gate opening effect of MAMS-1.
Figure 21:
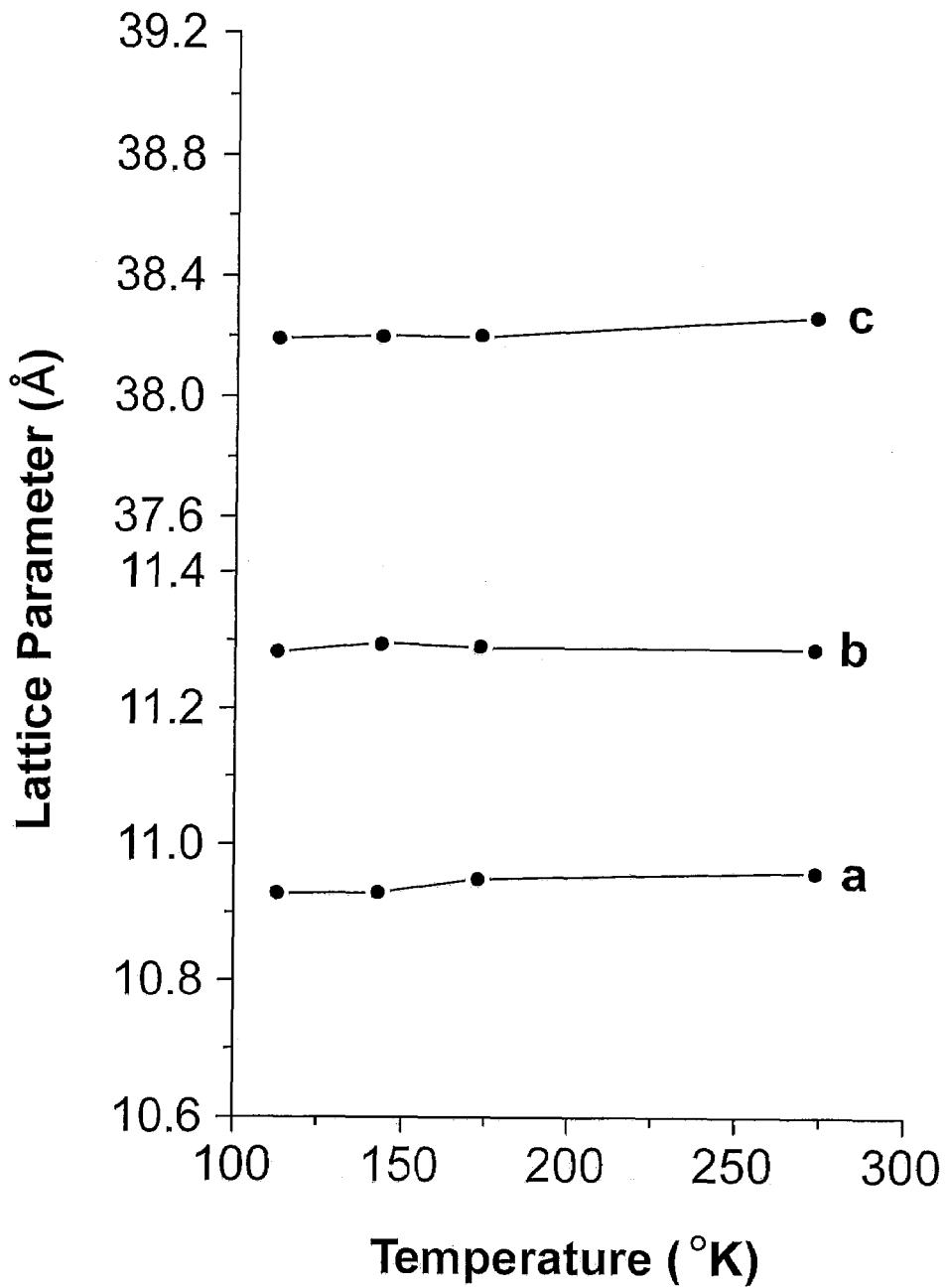
FIG. 21 illustrates cell various cell parameters at different temperatures for MAMS-1
Figure 2A:
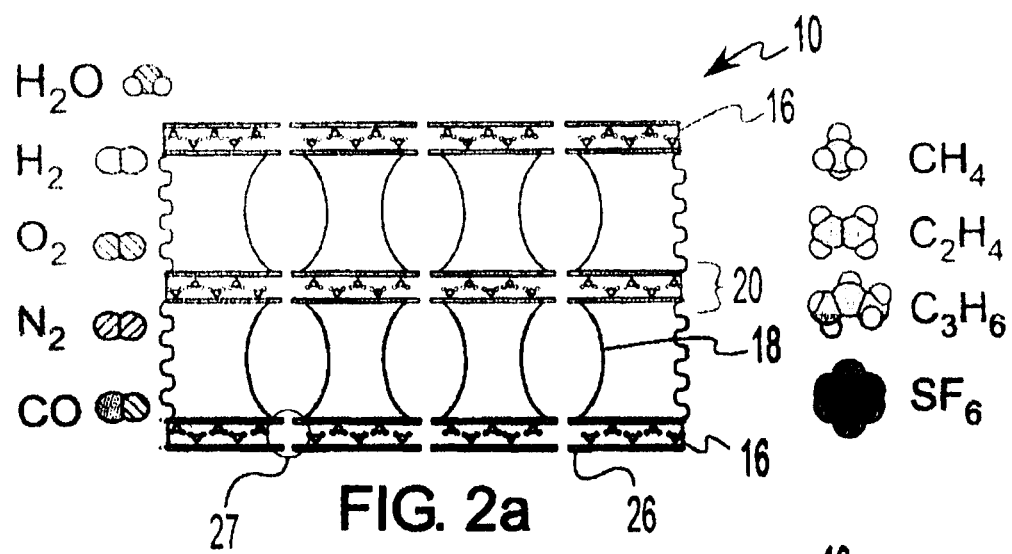
Figure 2B:
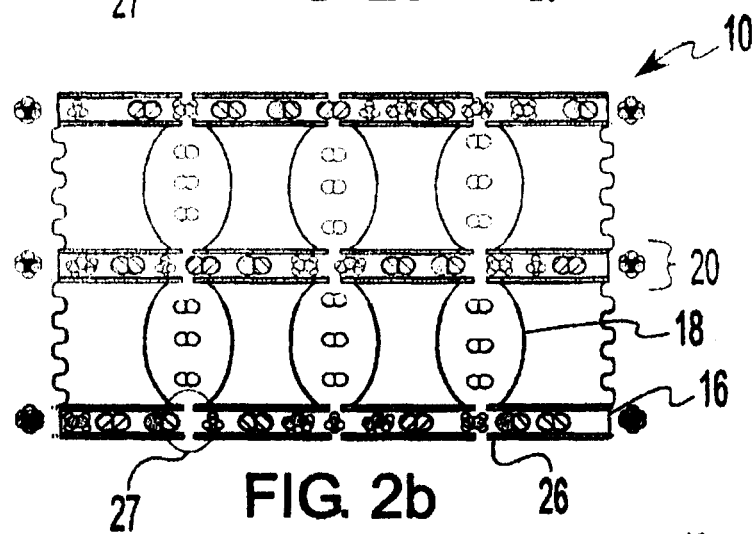
Figure 2C:
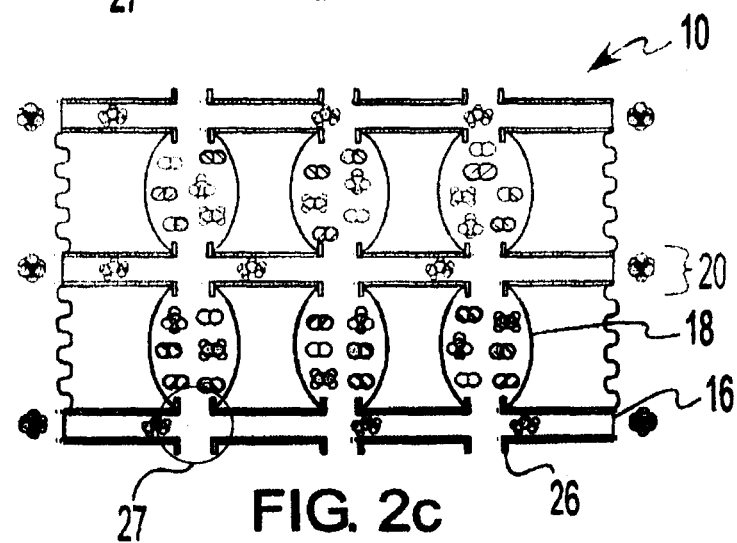
Figure 9E:
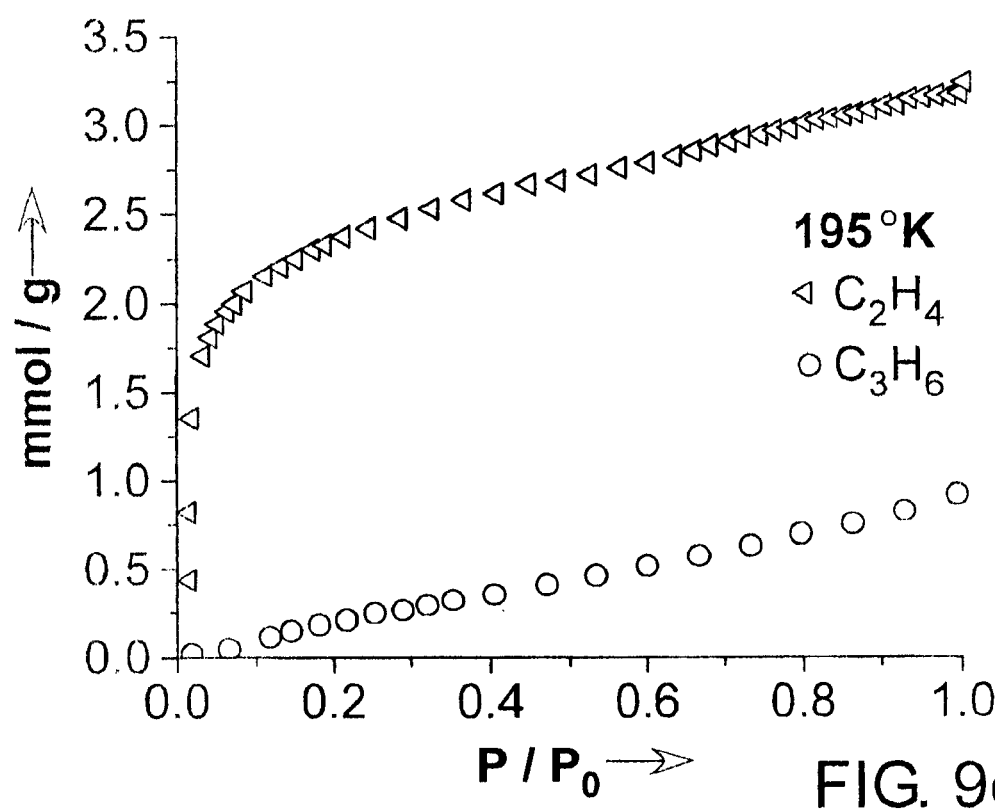
Figure 9F:
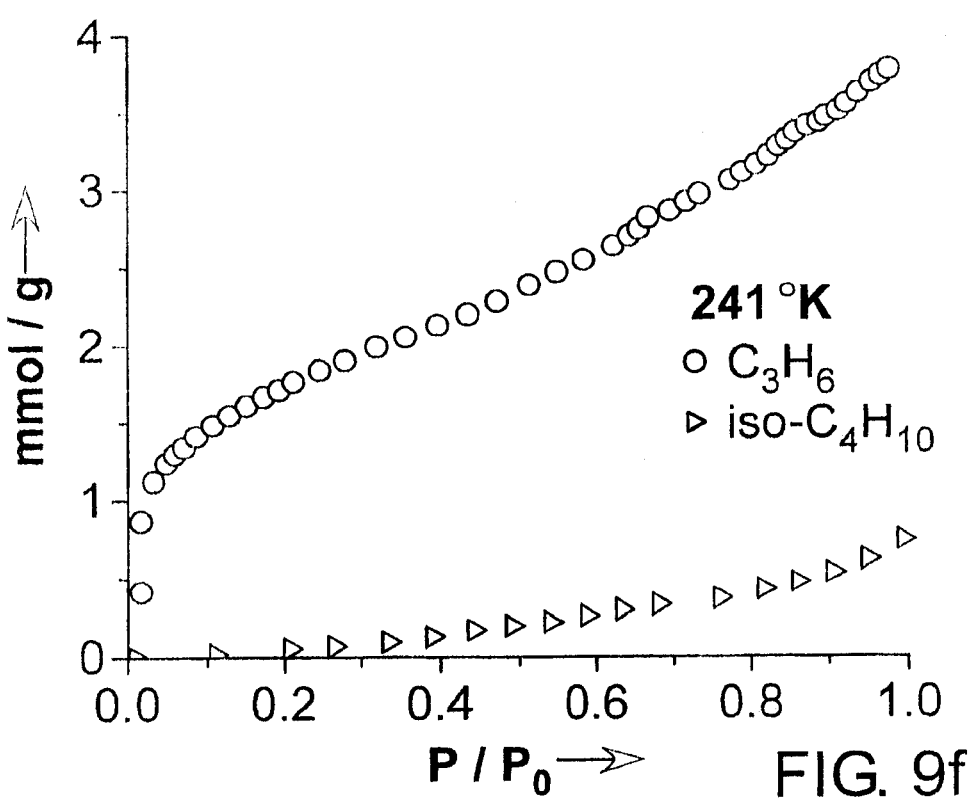

The temperature-dependent molecular-gating effect does not appear to arise from simple thermal expansion of the MAMS 10 framework. As shown in FIG. 21, for example, the lattice size parameters for $Ni_8(\mu_3\text{-}OH)_4(BBDC)_6$ (MAMS-1) 10 show virtually no response to temperature over a wide range. The opening of the gate 26 appears to be controlled by the amplitude of thermal vibration. FIG. 20, for example, shows temperature versus size of the molecule allowed to pass through the gate opening for MAMS-1 10. The data point in FIG. 20 at 77 deg. K gives an under-estimation of the gate opening because a gas molecule with a size between 2.89 Å ($H_2$) and 3.40 Å ($Ar$) is not available for gas adsorption studies. Ignoring the point at 77 deg. K, the gate opening D in Angstroms, and temperature T deg. K, and be related by a linear equation $$D = 0.0076\,T + 2.76,$$

with a correlation coefficient of 0.996. This equation can be used to predict if a gas molecule will be able to enter the gate 26 at a certain temperature. It may also be used to find the best temperature for the separation of a mixture. More generally, the linear relationship between mesh size and temperature can be represented as $$D = D_0 + \alpha T,$$

where D is the mesh size in Angstroms at temperature T (deg. K), $D_0$ is the mesh size in Angstroms at 0 deg. K, and $\alpha$ is a constant.

In synthesizing a MOF-based MAMS 10, a source of metal ions and a source of amphiphilic ligands (FIGS. 8a-8e), each ligand comprising a hydrophobic moiety 14 and a functionalized hydrophilic moiety (FIGS. 8a-8e), are mixed together in a first suitable solvent. The mixture is then heated to a first temperature, optionally at a first heating rate, held at the first temperature for a suitable length of time, and cooled to a second temperature, whereby MAMS are synthesized. Suitable solvents include, but are not limited to, $H_2O$/ethylene glycol, dimethyl sulfoxide (DMSO), dimethylacetamide (DMA), and dimethylformamide (DMF). First temperatures range, for example, between 75 deg. C. to 210 deg. C. Suitable hold temperatures range, for example, between 18 hours and 24 hours. After washing, the fresh MAMS are activated by suitable heating and pressure to remove guest solvent molecules and bound solvent molecules.

EXAMPLE

The MAMS illustrated in FIG. 1a (MAMS-1) was synthesized by a solvothermal reaction between $Ni(NO_3)_2$ and 5-tert-butyl-1,3-benzenedicarboxylate (BBDC). 5-tert-butyl-1,3-benzenedicarboxylic acid ($H_2BBDC$), (0.075 g, 0.34 mmol) and $Ni(NO_3)_2 \cdot 6H_2O$ (0.15 g, 0.51 mmol) in 7.5 ml $H_2O$/ethylene glycol (volume ratio 4:1) were placed in a 20 ml Teflon® (E. I. du Pont de Nemours and Company, Wilmington, Del.) container and sealed in an autoclave. The autoclave was heated to 210 deg. C. (heating rate 2 deg. C./min) in a programmable oven at which it stayed for 24 hours before being cooled to room temperature (cooling rate 0.5 deg. C./min). The light green needle-like crystals obtained were washed with distilled water and methanol to give pure MAMS-1 with the formula $Ni_8(\mu_3\text{-}OH)_4(C_{12}H_{12}O_4)_6(H_2O)_8 \cdot 8H_2O$ (55 percent yield based on $H_2BBDC$). Elemental analysis, calculated (percent): C, 40.28; H, 5.07; O, 32.79; found: C, 40.69; H, 5.07; O, 33.05. IR ($cm^{-1}$): 3305 (w, br), 2960 (m), 1033 (s), 865 (s), 785 (m).

Figure 11:
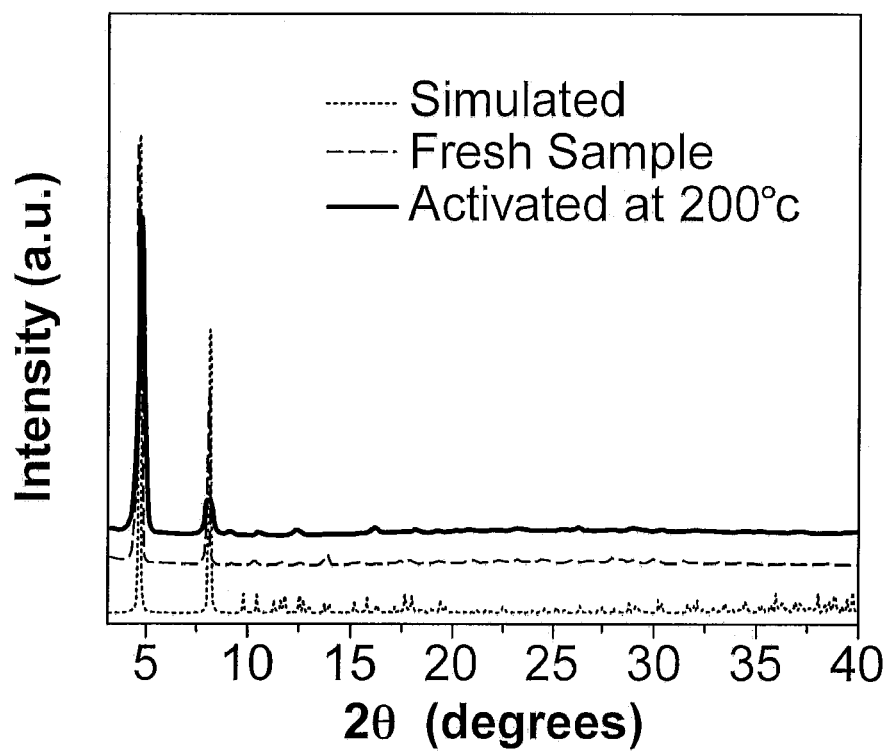
FIG. 11 illustrates X-ray powder diffraction patterns for fresh MAMS-1 and MAMS-1 activated at 200 deg. C.

Single crystal X-ray determination (FIG. 11) was performed on a Bruker Smart Apex® diffractometer (Bruker AXS, Inc., Madison, Wis.) using Mo—K$\alpha$ radiation ($\lambda = 0.71073$ Å). The data were collected on a crystal with dimensions of 0.23 mm×0.08 mm at −60 deg. C. A total of 1321 frames of data were collected using $\omega$-scans with an increment of 0.3 deg. and a counting time of 60 sec/frame. The raw data were processed using SAINT+® (Bruker) to yield the HKL file. Adsorption corrections were applied using SADABS® (Bruker). Direct methods were used to solve the structure, which was refined by full-matrix least-squares on $F^2$ with anisotropic displacement parameters. The hydrogen atoms on carbon and oxygen atoms were calculated in ideal positions with isotropic displacement parameters set to $1.2 * U_{eq}$ of the attached atom.

| Crystal Data - MAMS-1 | |
| --- | --- |
| Empirical formula | $C_{36}H_{52}Ni_4O_{21}$ |
| Formula weight | 1055.62 |
| Temperature | 213(2) K |
| Wavelength | 0.71073 Å |
| Crystal system, space group | Monoclinic, P2(1)/c |
| Unit cell dimensions | a = 10.9685 (2) Å alpha = 90.00°; |
| | b = 11.308 (2) Å beta = 96.781(3)°; |
| | c = 38.405 (7) Å gamma = 90.00°. |

-continued

Crystal Data - MAMS-1

| | |
|---|---|
| Volume | 4730.1(14) Å$^3$ |
| Z, Calculated density | 4, 1.482 g/cm$^3$ |
| Absorption coefficient | 1.641 mm$^{-1}$ |
| F(000) | 2192 |
| Crystal size | 0.23 × 0.08 × 0.08 mm |
| Theta range for data collection | 1.87 to 23.33° |
| Reflections collected/unique | 16860/6818 [R(int) = 0.0668] |
| Completeness to theta = 18.91 | 99.2% |
| Absorption correction | Empirical |
| Max. and min. transmission | 1.000 and 0.648 |
| Refinement method | Full-matrix least-squares on F$^2$ |
| Data/restraints/parameters | 6818/18/581 |
| Goodness-of-fit on F^2 | 1.021 |
| Final R indices [I>2sigma(I)] | R$_1$ = 0.0609, wR$_2$ = 0.1456 |
| R indices (all data) | R$_1$ = 0.0928, wR$_2$ = 0.1624 |

Thermogravimetric analysis (TGA) of MAMS-1 (9.8 mg) was performed with a Perkin-Elmer TGA 7 Thermogravimetric Analyzer under 50.0 ml/min flow of N$_2$. (FIG. 10.) The first weight loss of 6.72 percent (calculated: 6.71 percent) from 50 deg. C. to 120 deg. C. corresponds to the loss of eight free H$_2$O molecules, followed by the weight loss of 6.42 percent (calculated: 6.71 percent) corresponding to eight coordinated H$_2$O molecules from 120 deg. C. to 250 deg. C. Beyond 400 deg/C., the framework decomposes completely.

Figure 12:
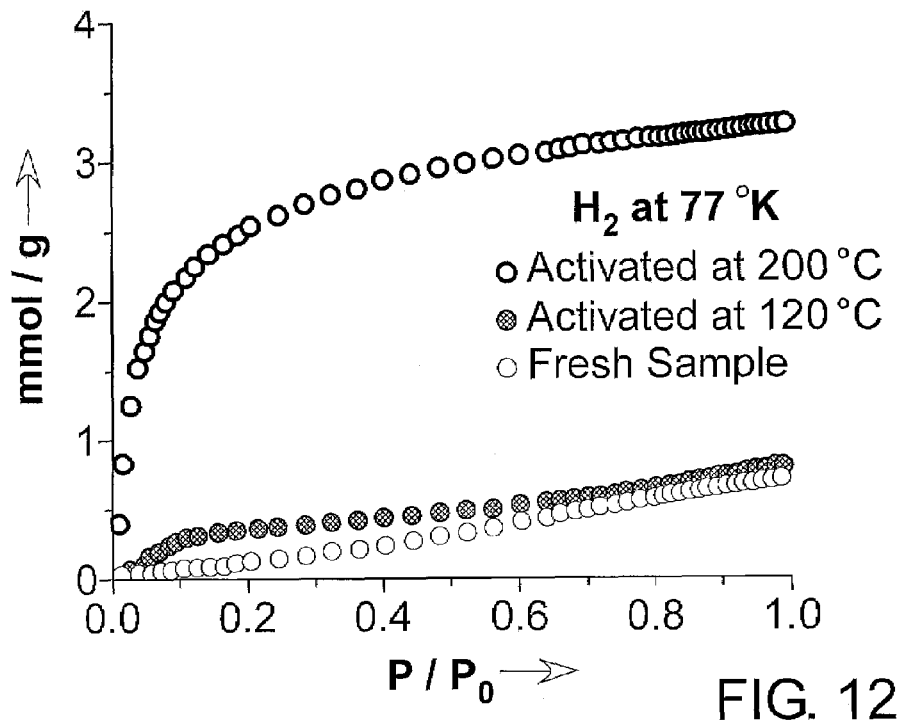
FIG. 12 illustrates $H_2$ adsorption isotherms at 77 deg. K for fresh MAMS-1, MAMS-1 activated at 120 deg. C., and MAMS-1 activated at 200 deg. C.
Figure 13:
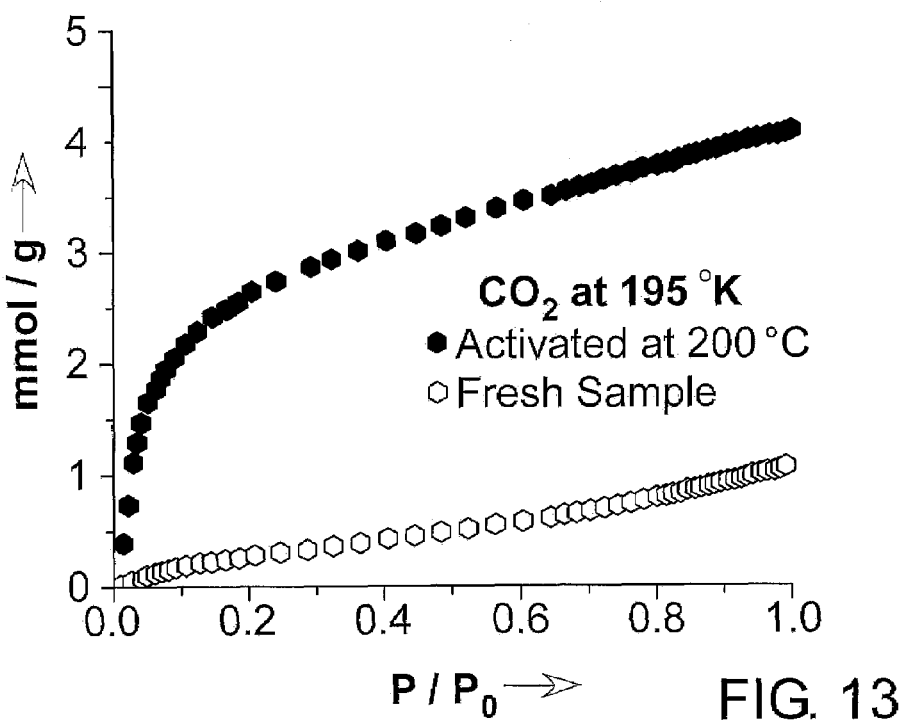
FIG. 13 illustrates $CO_2$ adsorption isotherms at 195 deg. K for fresh MAMS-1 and MAMS-1 activated at 200 deg. C.
Figure 14:
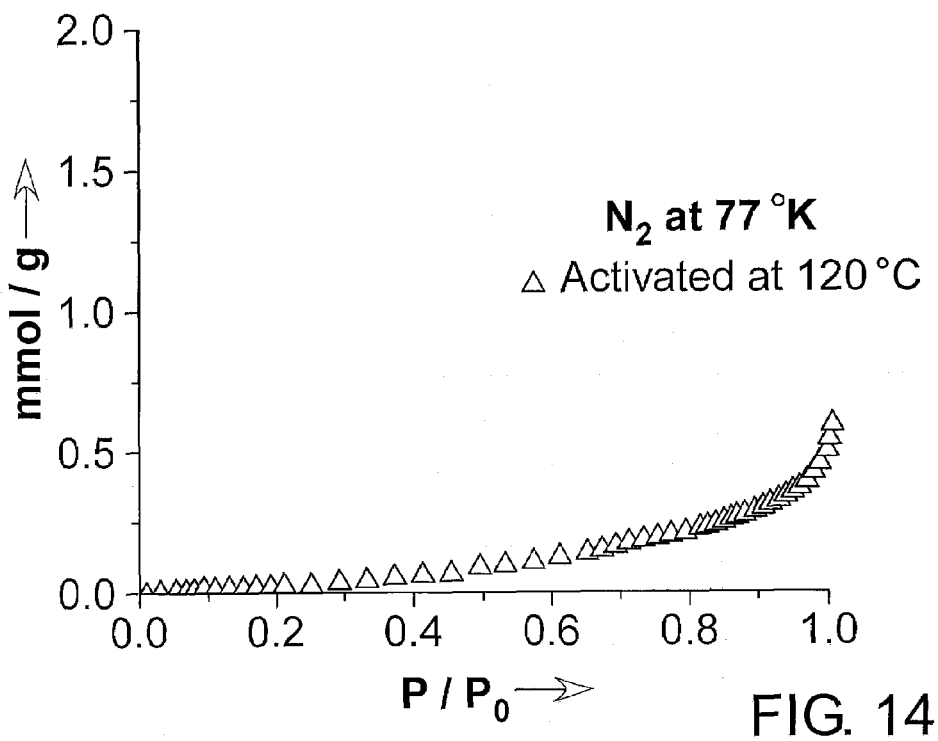
FIG. 14 illustrates a $N_2$ adsorption isotherm at 77 deg. K for MAMS-1 activated at 120 deg. C.
Figure 15:
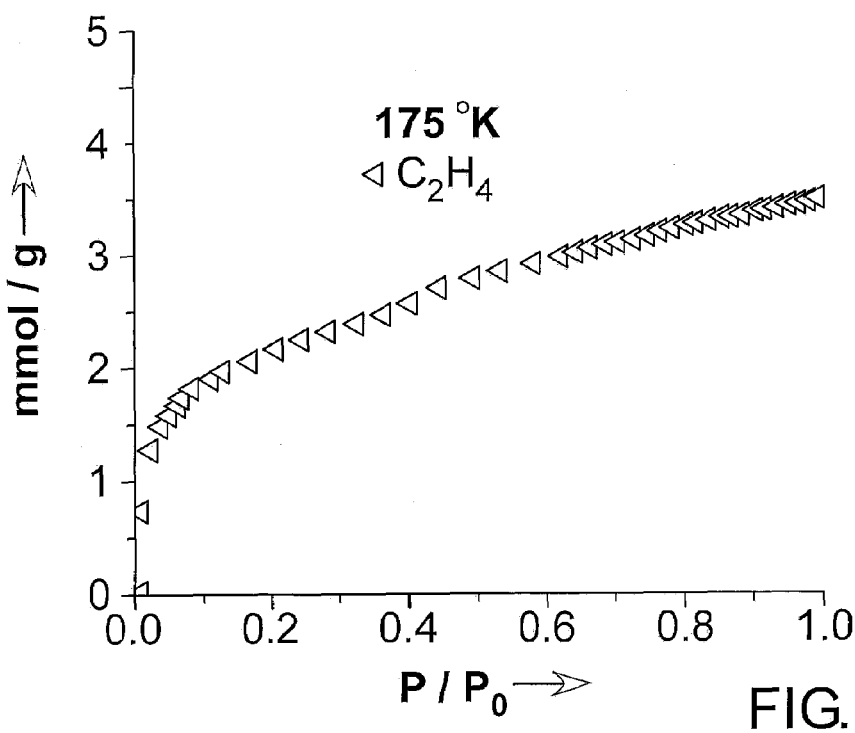
FIG. 15 illustrates a $C_2H_4$ adsorption isotherm at 175 deg. K for MAMS-1.
Figure 17:
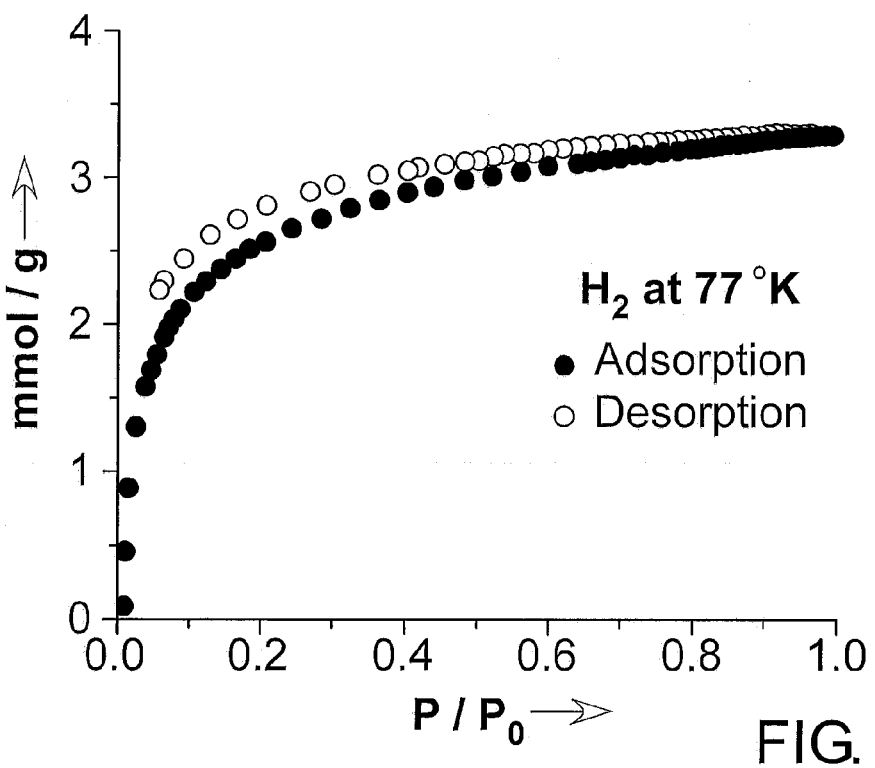
FIG. 17 illustrates $H_2$ sorption isotherms (adsorption and desorption) at 77 deg. K for MAMS-1.
Figure 18:
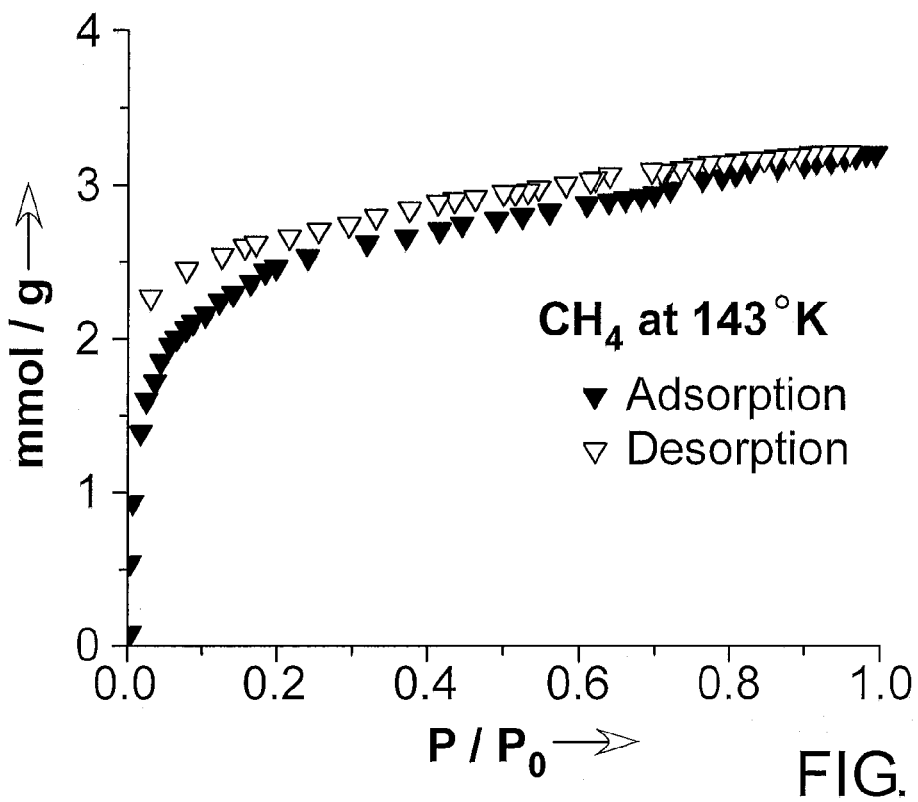
FIG. 18 illustrates $CH_4$ sorption isotherms (adsorption and desorption) at 143 deg. K for MAMS-1.
Figure 19:
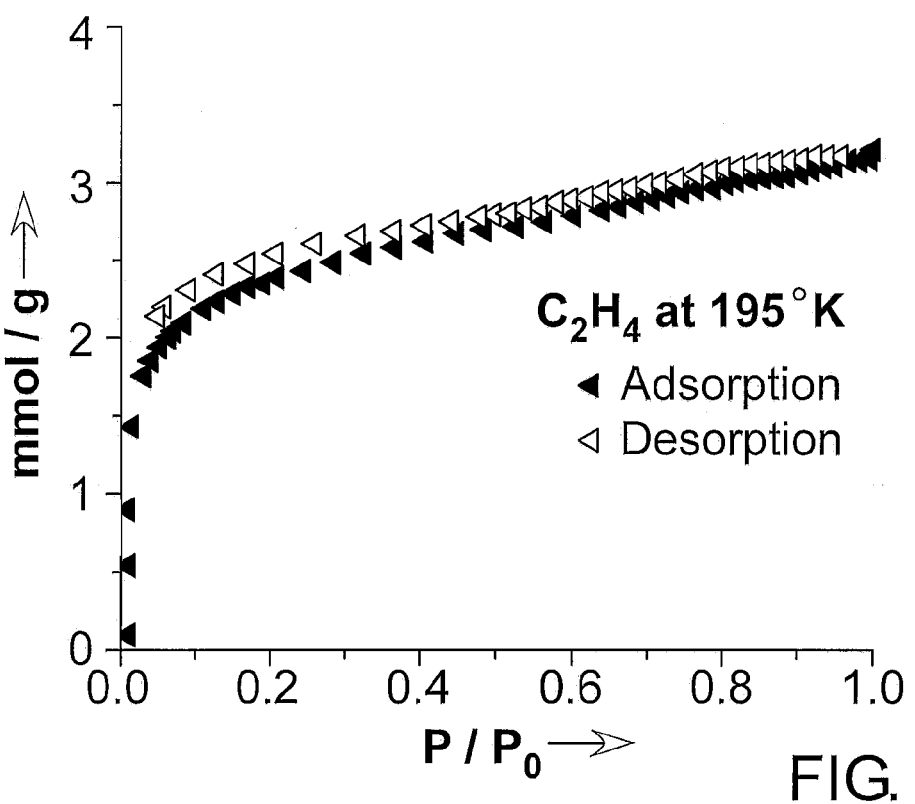
FIG. 19 illustrates $C_2H_4$ sorption isotherms (adsorption and desorption) at 195 deg. K for MAMS-1.

Gas adsorption measurements were measured with an SA 3100 surface area and pore size analyzer (Beckman Coulter, Inc., Fullerton, Calif.). The sample was held under dynamic vacuum (<10$^{-3}$ Torr) at 200 deg. C. overnight to remove the free and coordinated water molecules. Before the measurement, the sample was evacuated again by using the "outgas" function of the surface area analyzer for one hour at 200 deg. C. A sample of 40.0 mg was used for N$_2$ (99.999 percent) adsorption measurement, and was maintained at 77K with liquid nitrogen. (FIG. 9a.) In the H$_2$ adsorption measurement, high purity hydrogen (99.9995 percent) and a 40.0 mg sample were used. The regulator and pipe were flushed with hydrogen before connecting to the analyzer. The internal lines of the instrument were flushed three times by utilizing the "flushing lines" function of the program to ensure the purity of hydrogen. The measurement was maintained at 77 deg. K with liquid nitrogen. (FIGS. 12 and 17.) Similar to the procedures used for H$_2$ measurement at 77 K, highly pure O$_2$ (99.99 percent) (FIG. 9a), CO (99.99 percent) (FIG. 9a), CH$_4$ (99.997 percent) (FIG. 18), C$_2$H$_4$ (99.5 percent) cent) (FIG. 15 (175 deg. K) and 19 (195 deg. K)), C$_3$H$_6$ (99.5%) (FIGS. 9c and 9f), iso-C$_4$H$_{10}$ (99.5 percent) (FIG. 16), SF$_6$ (99.8 percent) (FIG. 16) and CO$_2$ (99.99 percent) (FIG. 13) were used for their respective gas adsorption measurements. All the gases used for the measurements were purchased from Linde Gas LLC, Cincinnati, Ohio. To prevent condensation of CO and O$_2$ at 77 K, the pressure ranges were below 448 Torr and 156 Torr, respectively. To prevent condensation of O$_2$ at 87 K, the pressure range was below 466 Torr. To prevent condensation of C$_2$H$_4$ at 143 K, the pressure range was below 120 Torr. To prevent condensation of C$_3$H$_6$ at 195 K, the pressure range was below 110 Torr. To prevent condensation of iso-C$_4$H$_{10}$ at 241 K, the pressure range was below 210 Torr. For all adsorption isotherms, P$_0$ represents a relative saturation pressure given by the SA 3100 during the measurements. At 77 deg. K, P$_0$ was 757 Torr for H$_2$ (FIG. 12) and N$_2$, 441 Torr for CO, and 151 Torr for O$_2$. At deg. 87 K, P$_0$ was 757 Torr for CO and N$_2$ and 465 Torr for O$_2$. At 113 deg. K, P$_0$ was 757 Torr for CO, CH$_4$, and N$_2$. At 143 deg. K, P$_0$ was 757 Torr for CH$_4$ and 118 Torr for C$_2$H$_4$. At 175 deg. K, P$_0$ was 757 Torr for C$_2$H$_4$. At 195 deg. K, P$_0$ was 757 Torr for C$_2$H$_4$ and CO$_2$ and 108 Torr for C$_3$H$_6$. At 241 deg. K, P$_0$ was 757 Torr for C$_3$H$_6$ and 205 Torr for iso-C$_4$H$_{10}$. At 298 K, P$_0$ was 757 Torr for iso-C$_4$H$_{10}$ and SF$_6$.

Figure 9B:
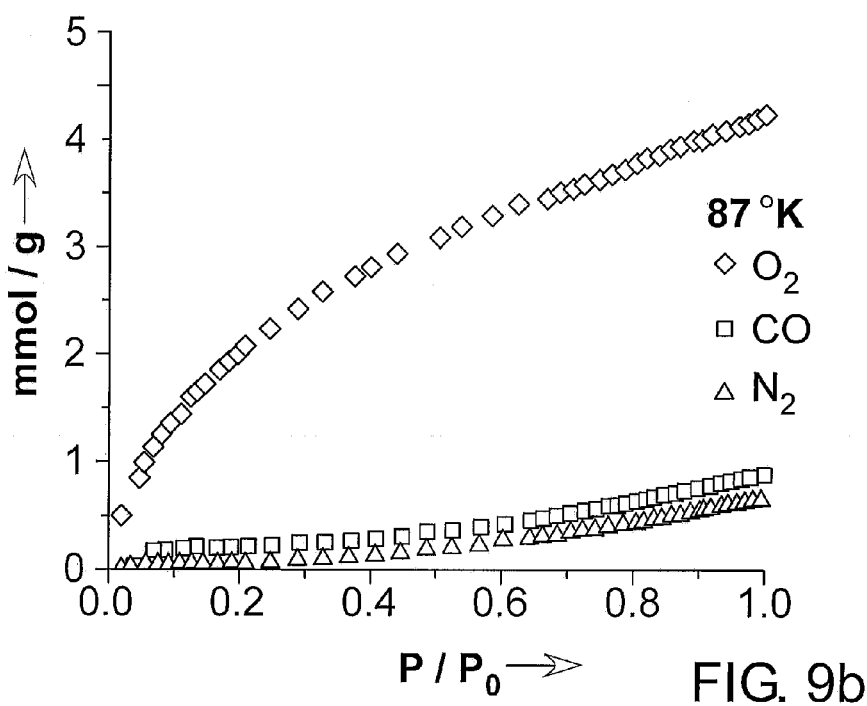

Referring now to FIG. 9a, at 77 deg. K, MAMS-1 excludes CO, N$_2$, and O$_2$, but allows H$_2$ to be adsorbed. When the temperature is raised to the temperature of liquid argon (87 deg. K), FIG. 9b shows that only a small amount of CO or N$_2$ is adsorbed by MAMS-1. At that temperature, however, MAMS-1 can take up a significant amount of O$_2$. The adsorption isotherm of O$_2$ shows typical Type-I behavior. Dioxygen (3.46 Å) can be selectively adsorbed from a mixture with N$_2$ (3.64 Å) and CO (3.76 Å), which would imply that at 87 deg. K, the gate 26 opens to about 3.5 Å.

Figure 9C:
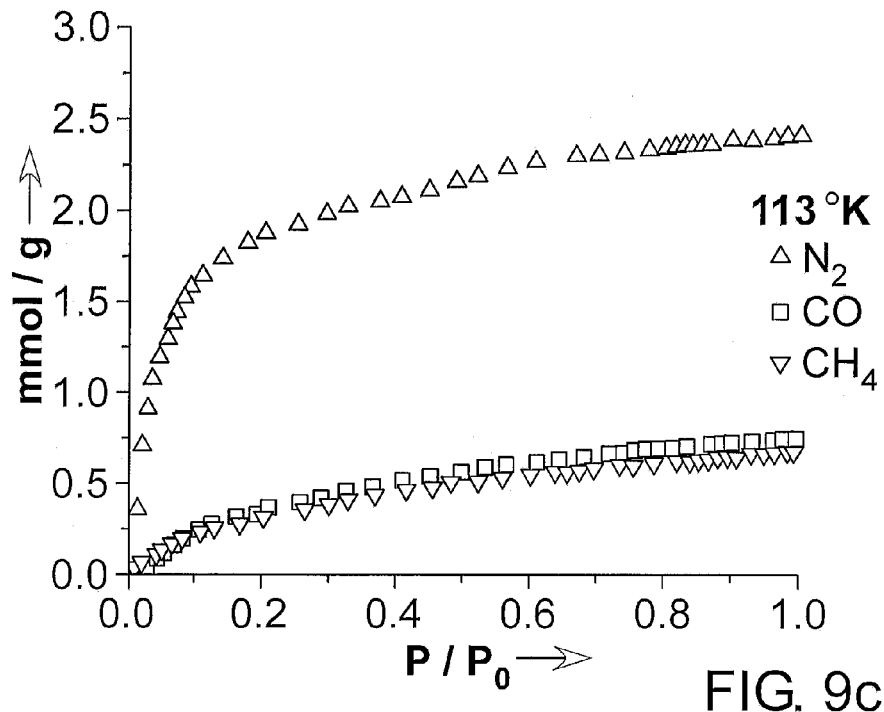

Referring now to FIG. 9c, at 113 deg. K, MAMS-1 can take up a moderate amount of N$_2$, but relatively low quantities of CO (3.76 Å) and CH$_4$ (3.8 Å). Thus, the gate 26 opens wide enough to enable N$_2$ (3.64 Å) to be adsorbed, but molecules with larger kinetic diameters such as CO and CH$_4$ are not.

Figure 9D:
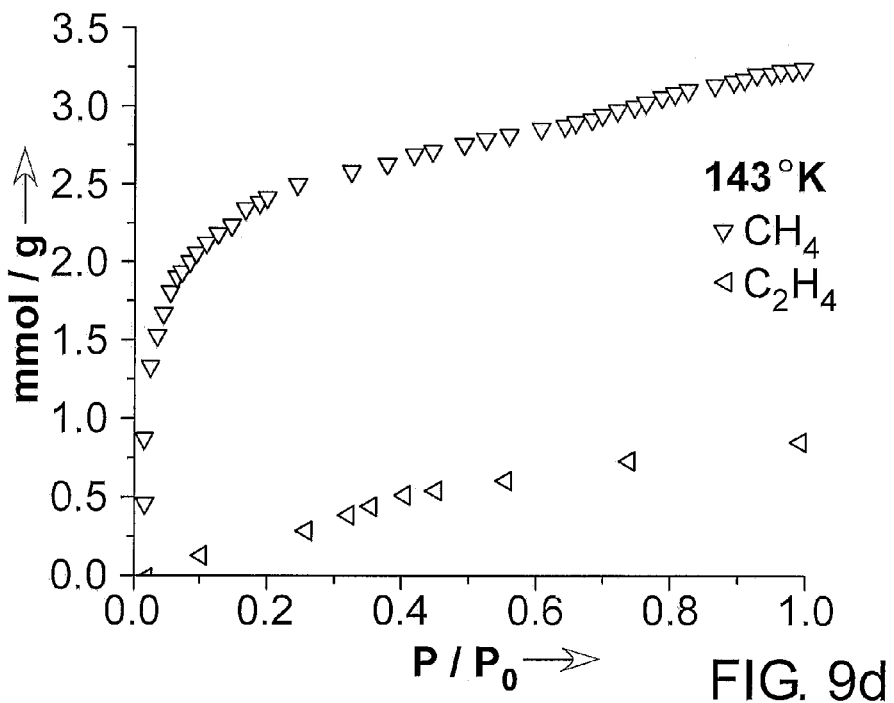
Figure 9E:
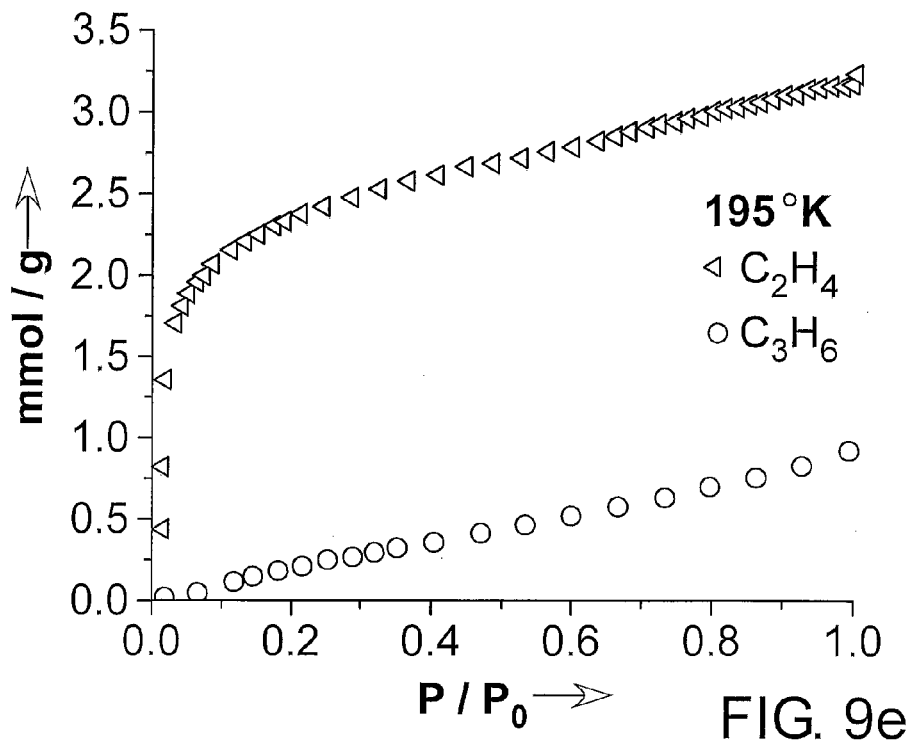
Figure 9F:
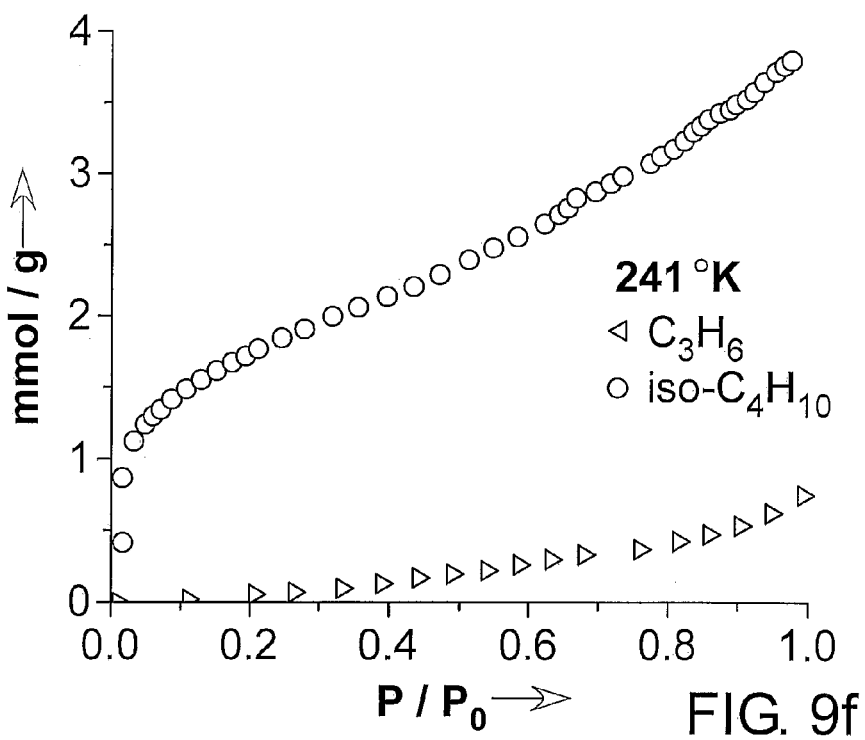

Referring now to FIG. 9d, MAMS-1 appears to distinguish between CH$_4$ and C$_2$H$_4$ (3.8 Å) at 143 deg. K. In addition, C$_2$H$_4$ is distinguished from C$_3$H$_6$ at 195 deg. K (FIG. 9e) and C$_3$H$_6$ (4.5 Å) from iso-C$_4$H$_{10}$ (5.0 Å) at 241 deg. K (FIG. 9f).

Figure 6:
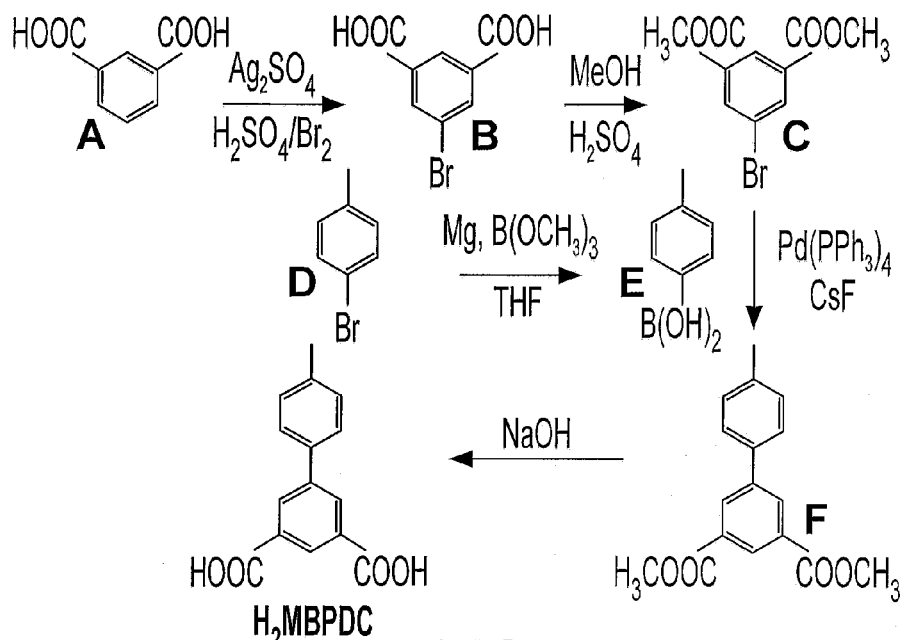
FIG. 6 is a ChemDraw® (Cambridge, Mass.) chemical structure drawing (ACS (American Chemical Society)-style) rendition of the synthesis of 4'-methyl-biphenyl-3,5-dicarboxylic acid ($H_2MBPDC$).

The 4'-methyl-biphenyl-3,5-dicarboxylic acid (H$_2$MBPDC) precursor for the ligand 4'-methyl-biphenyl-3,5-dicarboxylate (MBPDC) (FIG. 8a) is synthesized as shown in FIG. 6.

Figure 7:
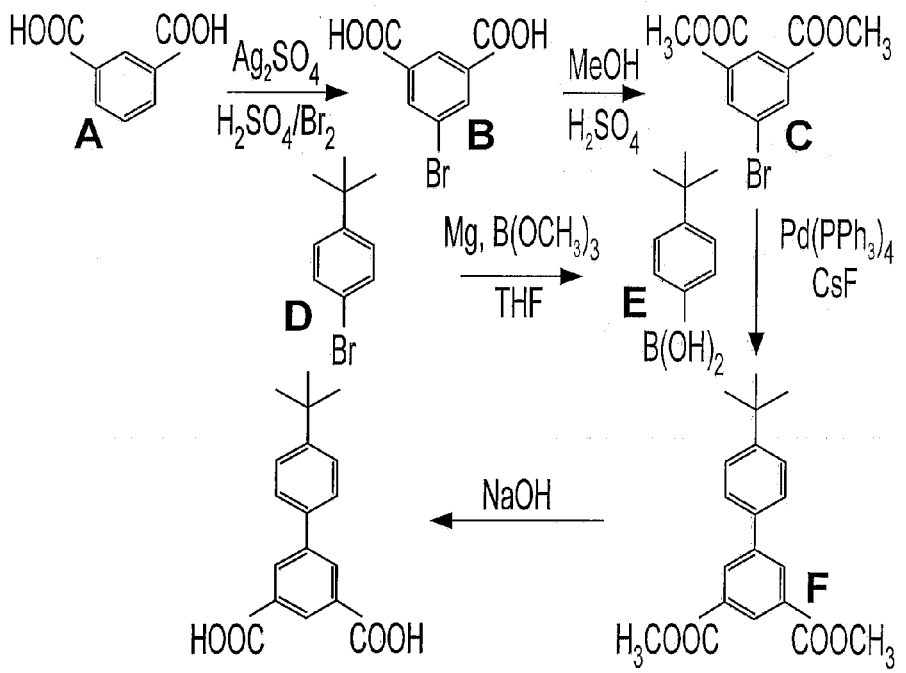
FIG. 7 is a ChemDraw® (Cambridge, Mass.) chemical structure drawing (ACS-style) rendition of the synthesis of 4'-tert-butyl-biphenyl-3,5-dicarboxylic acid ($H_2BBPDC$).
Figure 8A:
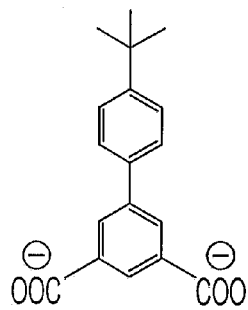
FIGS. 8a-8e are ChemDraw® (Cambridge, Mass.) chemical structure drawing (ACS-style) renditions of a number of exemplary ligands.
Figure 8A:
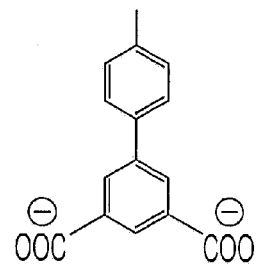
Figure 8A:
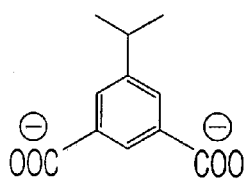
Figure 8A:
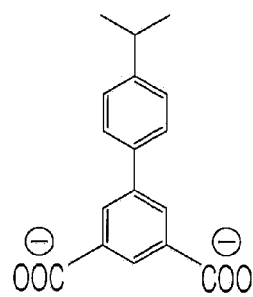
Figure 8A:
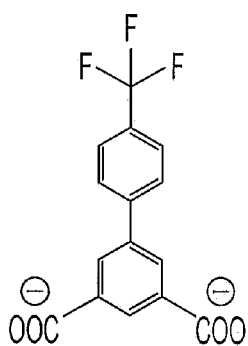
Figure 8B:
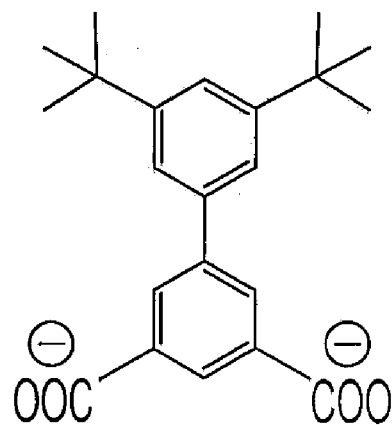
Figure 8B:
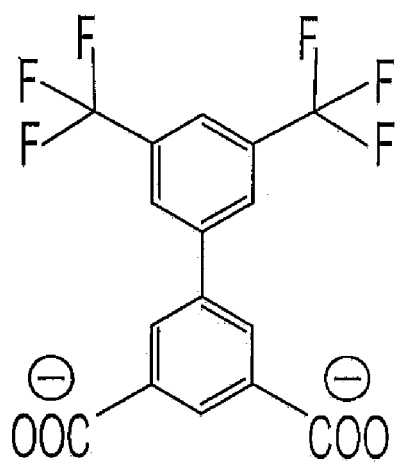
Figure 8C:
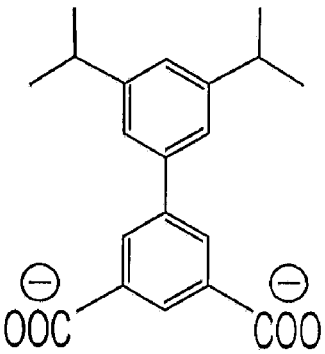
Figure 8C:
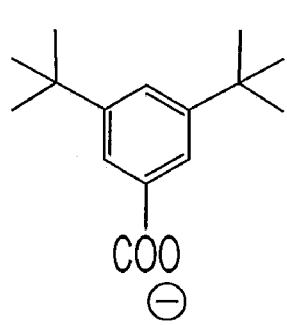
Figure 8C:
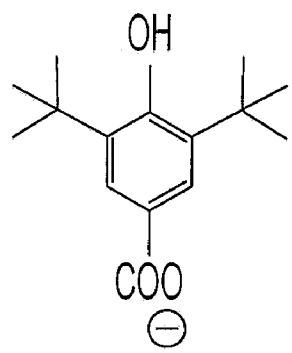
Figure 8C:
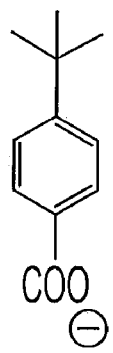
Figure 8C:
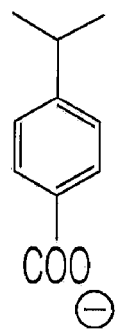
Figure 8D:
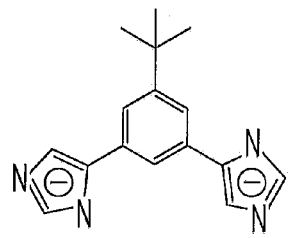
Figure 8D:
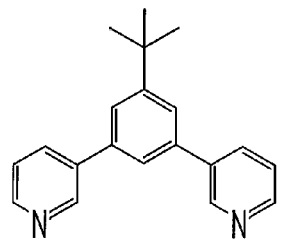
Figure 8D:
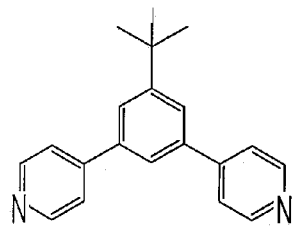
Figure 8D:
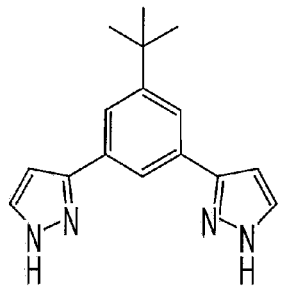
Figure 8D:
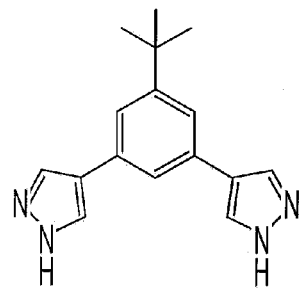
Figure 8E:
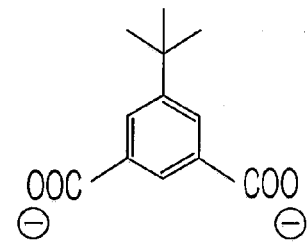
Figure 8E:
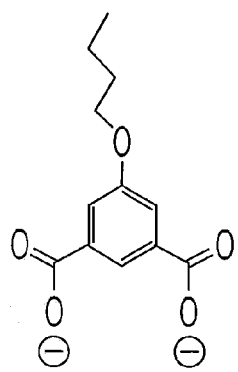
Figure 8E:
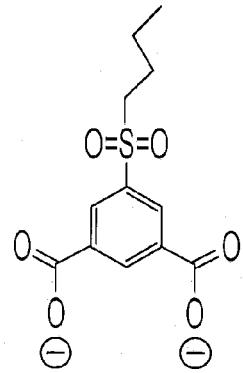
Figure 8E:
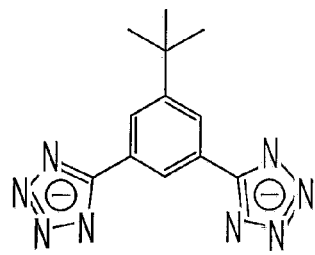

The 4'-tert-butyl-biphenyl-3,5-dicarboxylic acid (H$_2$BBPDC) precursor for the ligand 4'-tert-butyl-biphenyl-3,5-dicarboxylate (BBPDC) (FIG. 8a) is synthesized as shown in FIG. 7.

This detailed description in connection with the drawings is intended principally as a description of the presently preferred embodiments of the invention, and is not intended to represent the only form in which the present invention may be synthesized, formed, or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A metal-organic framework-based mesh-adjustable molecular sieve (MAMS), comprising:
   a plurality of metal clusters;
   a plurality of amphiphilic ligands, each ligand comprising:
      a hydrophobic moiety; and
      a functionalized hydrophilic moiety; and
   wherein:
      a plurality of metal clusters are bound with a plurality of amphiphilic ligand functionalized hydrophilic moieties to form a metal cluster layer, the metal cluster layer forming at least one hydrophilic pore;
      on each side of the metal cluster layer, a plurality of associated amphiphilic ligand hydrophobic moieties cooperate with the metal cluster layer to form a tri-layer; and
      a plurality of tri-layers are packed in a facing, spaced-apart relationship to form at least one hydrophobic pore.

2. The MAMS of claim 1, wherein the MAMS exhibits a temperature-dependent mesh size.

3. The MAMS of claim 2, wherein the temperature-dependent mesh size varies between about 2.9 Å and about 5 Å.

4. The MAMS of claim 1, wherein the MAMS exhibits a temperature-dependent molecular gating effect.

5. The MAMS of claim 1, wherein the metal clusters comprise at least one ion of metals selected from the group consisting of transition metals.

6. The MAMS of claim 5, wherein the transition metals are selected from the group consisting of period four transition metals.

7. The MAMS of claim 6, wherein the period four transition metals are selected from the group consisting of Cr, Ni, Cu, Co, Mn, and Zn.

8. The MAMS of claim 5, wherein:
the transition metals are selected from the group consisting of Cr, Ni, Cu, Co, Mn, Zn, and Cd; and
the plurality of amphiphilic ligands comprise 4'-tert-butyl-biphenyl-3,5dicarboxylate (BBPDC).

9. The MAMS of claim 5, wherein:
the transition metals are selected from the group consisting of Cr, Ni, Cu, Co, Mn, Zn, and Cd; and
the plurality of amphiphilic ligands comprise 5-tert-butyl-1,3-benzene dicarboxylate (BBDC).

10. The MAMS of claim 5 wherein:
the transition metal is Cu; and
the plurality of amphiphilic ligands comprise 4'-methyl-biphenyl-3,5-dicarboxylate (MBPDC).

11. The MAMS of claim 1, wherein the metal clusters comprise at least one ion of metals selected from the group consisting of Al, Ge, and Ga.

12. The MAMS of claim 1, wherein the amphiphilic ligand is selected from the group consisting of:

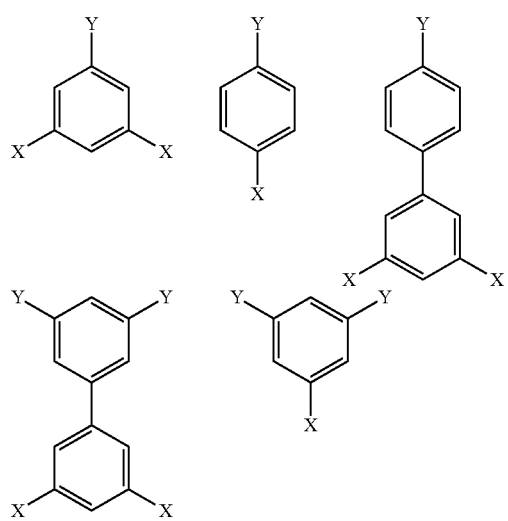

wherein:
X is at least one of carboxylate, cyano, phosphonate, sulfonate, imidazolate, pyridine, pyrazole, and tetrazolate; and
Y is at least one of tert-butyl, methyl, isopropyl, trifluoromethyl, butoxyl, and butylsulfonyl, alkyl, halogenated alkyl, alkenyl, alkynyl, and alkoxyl.

13. The MAMS of claim 1, wherein the at least one hydrophilic pore reaches the structural limits of the MAMS.

14. The MAMS of claim 1, wherein at least one hydrophobic moiety substantially faces at least one other hydrophobic moiety in a spaced-apart relationship.

15. The MAMS of claim 1, wherein the at least one hydrophilic pore exhibits an atom-to-atom distance of about 8 Angstroms (Å).

16. The MAMS of claim 15, wherein the at least one hydrophilic pore exhibits an atom-to-atom distance of about 5 Å considering van der Waals radii.

17. The MAMS of claim 1, wherein the plurality of metal clusters are coordinatively bound with the plurality of functionalized hydrophilic moieties.

18. The MAMS of claim 1, wherein the plurality of tri-layers pack in a graphitic structure.

19. A method of separating gaseous molecules, comprising contacting the MAMS of claim 1 with a mixture of molecules selected from the group consisting of $H_2/N_2$, $H_2/CO$, $N_2/O_2$, $N_2/CH_4$, $CH_4/C_2H_4$ and $C_2H_4/C_3H_6$, wherein the molecules are separated from their respective pair.

20. A method of adsorbing a molecular species selected from the group consisting of $H_2$, $N_2$, $O_2$, CO, Ar, $CH_4$, $C_2H_4$, and $C_3H_6$, comprising contacting the MAMS of claim 1 with a mixture of molecular species comprising one of $H_2$, $N_2$, $O_2$, CO, Ar, $CH_4$, $C_2H_4$, and $C_3H_6$.

21. The method of claim 20, wherein the adsorption temperature, T deg, K, is selected according to the equation D=0.0076 T+2.76, where D is the kinetic diameter, in Angstroms, of the molecular species of interest.

22. A metal-organic framework-based mesh-adjustable molecular sieve (MAMS), comprising:
a plurality of metal ions;
a plurality of amphiphilic ligands, each ligand comprising:
a hydrophobic moiety; and
a functionalized hydrophilic moiety; and
wherein:
a plurality of metal ions are bound with a plurality of amphiphilic ligand functionalized hydrophilic moieties to form a metal cluster layer, the metal cluster layer forming at least one hydrophilic pore;
on each side of the metal cluster layer, a plurality of associated amphiphilic ligand hydrophobic moieties cooperate with the metal cluster layer to form a tri-layer; and
a plurality of tri-layers are packed in a facing, spaced-apart relationship to form at least one hydrophobic pore.

23. The MAMS of claim 19, wherein the MAMS exhibits a temperature-dependent mesh size.

24. The MAMS of claim 23, wherein the temperature-dependent mesh size varies between about 2.9 Å and about 5 Å.

25. The MAMS of claim 22, wherein the MAMS exhibits a temperature-dependent molecular gating effect.

26. The MAMS of claim 22, wherein the metal ions are selected from the group consisting of transition metals.

27. The MAMS of claim 26, wherein the transition metals are selected from the group consisting of period four transition metals.

28. The MAMS of claim 27, wherein the period four transition metals are selected from the group consisting of Cr, Ni, Cu, Co, Mn, and Zn.

29. The MAMS of claim 26, wherein:
the transition metals are selected from the group consisting of Cr, Ni, Cu, Co, Mn, Zn, and Cd; and
the plurality of amphiphilic ligands comprise 4'-tert-butyl-biphenyl-3,5dicarboxylate (BBPDC).

30. The MAMS of claim 26, wherein:
the transition metals are selected from the group consisting of Cr, Ni, Cu, Co, Mn, Zn, and Cd; and the plurality of amphiphilic ligands comprise 5-tert-butyl-1,3-benzene dicarboxylate (BBDC).

31. The MAMS of claim 26 wherein:
the transition metal is Cu; and
the plurality of amphiphilic ligands comprise 4'-methyl-biphenyl-3,5-dicarboxylate (MBPDC).

32. The MAMS of claim 22, wherein the metal ions are selected from the group consisting of Al, Ge, and Ga.

33. The MAMS of claim 22, wherein the amphiphilic ligand is selected from the group consisting of:

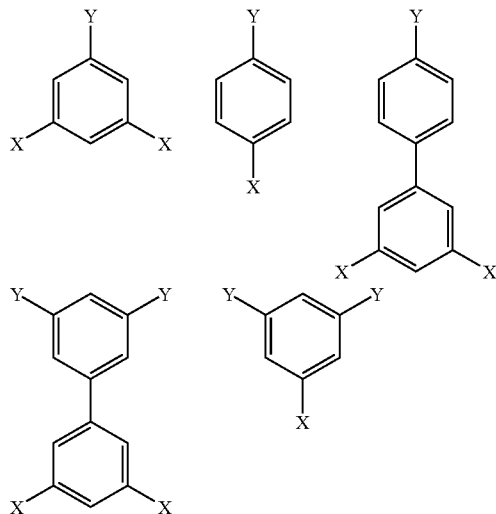

wherein:
X is at least one of carboxylate, cyano, phosphonate, sulphonate, imidazolate, pyridine, pyrazole, and tetrazolate; and
Y is at least one of tert-butyl, methyl, isopropyl, trifluoromethyl, butoxyl, and butylsulfonyl, alkyl, halogenated alkyl, alkenyl, alkynyl, and alkoxyl.

34. The MAMS of claim 22, wherein the at least one hydrophilic pore reaches the structural limits of the MAMS.

35. The MAMS of claim 22, wherein at least one hydrophobic moiety substantially faces at least one other hydrophobic moiety in a spaced-apart relationship.

36. The MAMS of claim 22, wherein the at least one hydrophilic pore exhibits an atom-to-atom distance of about 8 Angstroms (Å).

37. The MAMS of claim 36, wherein the at least one hydrophilic pore exhibits an atom-to-atom distance of about 5 Å considering van der Waals radii.

38. The MAMS of claim 22, wherein the plurality of metal ions are coordinatively bound with the plurality of functionalized hydrophilic moieties.

39. The MAMS of claim 22, wherein the plurality of tri-layers pack in a graphitic structure.

40. A method of separating gaseous molecules, comprising contacting the MAMS of claim 22 with a mixture of molecules selected from the group consisting of $H_2/N_2$, $H_2/CO$, $N_2/O_2$, $N_2/CH_4$, $CH_4/C_2H_4$ and $C_2H_4/C_3H_6$, wherein the molecules are separated from their respective pair.

41. A method of adsorbing a molecular species selected from the group consisting of $H_2$, $N_2$, $O_2$, CO, Ar, $CH_4$, $C_2H_4$, and $C_3H_6$, comprising contacting the MAMS of claim 22 with a mixture of molecular species comprising one of $H_2$, $N_2$, $O_2$, CO, Ar, $CH_4$, $C_2H_4$, and $C_3H_6$.

42. The method of claim 41, wherein the adsorption temperature, T deg. K, is selected according to the equation $D=D_0+\alpha T$, where D is the kinetic diameter, in Angstroms, of the molecular species of interest, $D_0$ is the kinetic diameter of a molecular species, in Angstroms, adsorbed at 0 deg. K, and $\alpha$ is a constant.

43. A metal-organic framework-based mesh-adjustable molecular sieve (MAMS) comprising:
a plurality of first secondary building units (SBUs), each first SBU comprising a metal cluster;
a plurality of second SBUs, each second SBU comprising an amphiphilic ligand, each ligand comprising:
a hydrophobic moiety; and
a functionalized hydrophilic moiety; and
wherein:
the functionalized hydrophilic moieties of at least two second SBUs are bound with at least one first SBU to form a tri-layer, each tri-layer forming at least one hydrophilic pore;
a plurality of tri-layers are packed in a facing, spaced-apart relationship to form at least one hydrophobic pore.

44. The MAMS of claim 43, wherein the MAMS exhibits a temperature-dependent mesh size.

45. The MAMS of claim 44, wherein the temperature-dependent mesh size varies between about 2.9 Å and about 5 Å.

46. The MAMS of claim 43, wherein the MAMS exhibits a temperature-dependent molecular gating effect.

47. The MAMS of claim 43, wherein the first SBU comprises $M_XA_Y$, wherein:
M is chosen from the group consisting of transition metals, Al, Ge, and Ga; and
A comprises moieties chosen from the group consisting of oxo, hydroxyl, aqua, sulfido, and halogen.

48. The MAMS of claim 43, wherein the first SBU comprises a cluster selected from the group consisting of $Ni_8(\mu_3-OH)_4$, $Cu_2$, $Co_2$, $Mn_2$, and $Zn_2$.

49. The MAMS of claim 43, wherein the second SBU comprises a compound selected from the group consisting of:

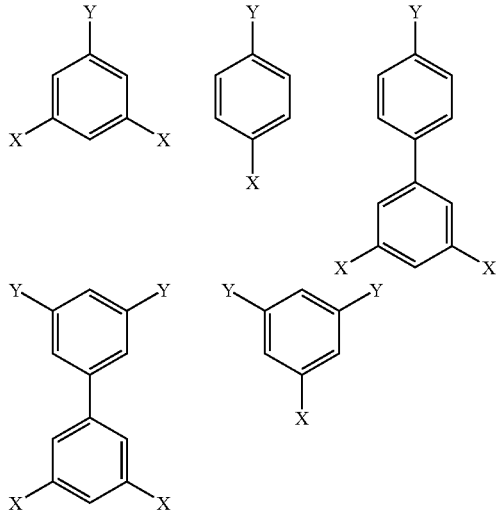

wherein:
X is at least one of carboxylate, cyano, phosphonate, sulfonate, imidazolate, pyridine, pyrazole, and tetrazolate; and Y is at least one of tert-butyl, methyl, isopropyl, trifluoromethyl, butoxyl, and butylsulfonyl, alkyl, halogenated alkyl, alkenyl, alkynyl, and alkoxyl.

50. The MAMS of claim 43, wherein the at least one hydrophilic pore reaches the structural limits of the MAMS.

51. The MAMS of claim 43, wherein at least one hydrophobic moiety substantially faces at least one other hydrophobic moiety in a spaced-apart relationship.

52. The MAMS of claim 43, wherein the at least one hydrophilic pore exhibits an atom-to-atom distance of about 8 Angstroms (Å).

53. The MAMS of claim 52, wherein the at least one hydrophilic pore exhibits an atom-to-atom distance of about 5 Å considering van der Waals radii.

54. The MAMS of claim 43, wherein the plurality of metal clusters are coordinatively bound with the plurality of functionalized hydrophilic moieties.

55. The MAMS of claim 43, wherein the plurality of tri-layers pack in a graphitic structure.

56. A method of separating gaseous molecules, comprising contacting the MAMS of claim 43 with a mixture of molecules selected from the group consisting of $H_2/N_2$, $H_2/CO$, $N_2/O_2$, $N_2/CH_4$, $CH_4/C_2H_4$ and $C_2H_4/C_3H_6$, wherein the molecules are separated from their respective pair.

57. A method of adsorbing a molecular species selected from the group consisting of $H_2$, $N_2$, $O_2$, CO, Ar, $CH_4$, $C_2H_4$, and $C_3H_6$, comprising contacting the MAMS of claim 43 with a mixture of molecular species comprising one of $H_2$, $N_2$, $O_2$, CO, Ar, $CH_4$, $C_2H_4$, and $C_3H_6$.

58. A metal-organic framework-based mesh-adjustable molecular sieve (MAMS) comprising:
    a plurality of first secondary building units (SBUs), each first SBU comprising at least one metal ion;
    a plurality of second SBUs, each second SBU comprising an amphiphilic ligand, each ligand comprising:
        a hydrophobic moiety; and
        a functionalized hydrophilic moiety; and
    wherein:
        the functionalized hydrophilic moieties of at least two second SBUs are bound with at least one first SBU to form a tri-layer, each tri-layer forming at least one hydrophilic pore;
        a plurality of tri-layers are packed in a facing, spaced-apart relationship to form at least one hydrophobic pore.

59. The MAMS of claim 58, wherein the MAMS exhibits a temperature-dependent mesh size.

60. The MAMS of claim 59, wherein the temperature-dependent mesh size varies between about 2.9 Å and about 5 Å.

61. The MAMS of claim 58, wherein the MAMS exhibits a temperature-dependent molecular gating effect.

62. The MAMS of claim 58, wherein the at least one metal ion is selected from the group consisting of transition metals.

63. The MAMS of claim 62, wherein the transition metals are selected from the group consisting of period four transition metals.

64. The MAMS of claim 63, wherein the period four transition metals are selected from the group consisting of Cr, Ni, Cu, Co, Mn, and Zn.

65. The MAMS of claim 62, wherein:
    the transition metals are selected from the group consisting of Cr, Ni, Cu, Co, Mn, Zn, and Cd; and
    the plurality of amphiphilic ligands comprise 4'-tert-butyl-biphenyl-3,5dicarboxylate (BBPDC).

66. The MAMS of claim 62, wherein:
    the transition metals are selected from the group consisting of Cr, Ni, Cu, Co, Mn, Zn, and Cd; and
    the plurality of amphiphilic ligands comprise 5-tert-butyl-1,3-benzene dicarboxylate (BBDC).

67. The MAMS of claim 62 wherein:
    the transition metal ion is Cu; and
    the amphiphilic ligand comprises 4'-methyl-biphenyl-3,5-dicarboxylate (MBPDC).

68. The MAMS of claim 58, wherein the metal ion is selected from the group consisting of Al, Ge, and Ga.

69. The MAMS of claim 58, wherein the amphiphilic ligand is selected from the group consisting of:

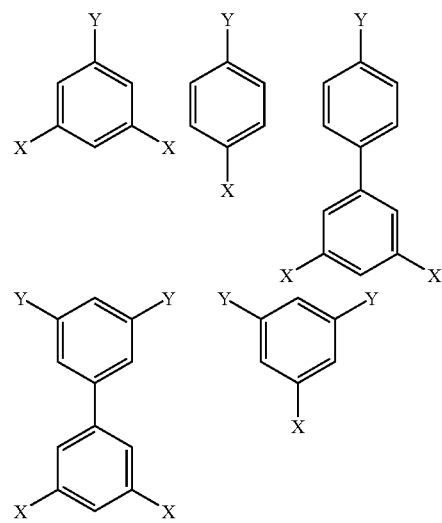

wherein:
    X is at least one of carboxylate, cyano, and phosphonate, sulfonate, imidazolate, pyridine, pyrazole, and tetrazolate; and
    Y is at least one of tert-butyl, methyl, isopropyl, trifluoromethyl, butoxyl, and butylsulfonyl, alkyl, halogenated alkyl, alkenyl, alkynyl, and alkoxyl.

70. The MAMS of claim 58, wherein the at least one hydrophilic pore reaches the structural limits of the MAMS.

71. The MAMS of claim 58, wherein at least one hydrophobic moiety substantially faces at least one other hydrophobic moiety in a spaced-apart relationship.

72. The MAMS of claim 58, wherein the at least one hydrophilic pore exhibits an atom-to-atom distance of about 8 Angstroms (Å).

73. The MAMS of claim 72, wherein the at least one hydrophilic pore exhibits an atom-to-atom distance of about 5 Å considering van der Waals radii.

74. The MAMS of claim 58, wherein the plurality of metal ions are coordinatively bound with the plurality of functionalized hydrophilic moieties.

75. The MAMS of claim 58, wherein the plurality of tri-layers pack in a graphitic structure.

76. A method of separating gaseous molecules, comprising contacting the MAMS of claim 58 with a mixture of molecules selected from the group consisting of $H_2/N_2$, $H_2/CO$, $N_2/O_2$, $N_2/CH_4$, $CH_4/C_2H_4$ and $C_2H_4/C_3H_6$, wherein the molecules are separated from their respective pair.

77. A method of adsorbing a molecular species selected from the group consisting of $H_2$, $N_2$, $O_2$, CO, Ar, $CH_4$, $C_2H_4$, and $C_3H_6$, comprising contacting the MAMS of claim 58 with a mixture of molecular species comprising one of $H_2$, $N_2$, $O_2$, CO, Ar, $CH_4$, $C_2H_4$, and $C_3H_6$.

78. A metal-organic framework-based mesh-adjustable molecular sieve (MAMS) comprising:
a plurality of tri-layers, each tri-layer comprising:
two layers of amphiphilic ligands, each ligand comprising:
a hydrophobic moiety; and
a functionalized hydrophilic moiety;
a layer of metal clusters sandwiched between the two ligand layers; and
wherein:
the functionalized hydrophilic moieties are bound to metal clusters to form at least one hydrophilic pore; and
at least two tri-layers are packed in a facing, spaced-apart relationship to form at least one hydrophobic pore.

79. The MAMS of claim 78, wherein the MAMS exhibits a temperature-dependent mesh size.

80. The MAMS of claim 79, wherein the temperature-dependent mesh size varies between about 2.9 Å and about 5 Å.

81. The MAMS of claim 78, wherein the MAMS exhibits a temperature-dependent molecular gating effect.

82. The MAMS of claim 78, wherein the metal clusters comprise at least one ion of metals selected from the group consisting of transition metals.

83. The MAMS of claim 82, wherein the transition metals are selected from the group consisting of period four transition metals.

84. The MAMS of claim 83, wherein the period four transition metals are selected from the group consisting of Cr, Ni, Cu, Co, Mn, and Zn.

85. The MAMS of claim 82, wherein:
the transition metals are selected from the group consisting of Cr, Ni, Cu, Co, Mn, Zn, and Cd; and
the plurality of amphiphilic ligands comprise 5-tert-butyl-1,3-benzene dicarboxylate (BBDC).

86. The MAMS of claim 82, wherein:
the transition metals are selected from the group consisting of Cr, Ni, Cu, Co, Mn, Zn, and Cd; and
the plurality of amphiphilic ligands comprise 4'-tert-butyl-biphenyl-3,5dicarboxylate (BBPDC).

87. The MAMS of claim 82 wherein:
the transition metal is Cu; and
the amphiphilic ligands comprise 4'-methyl-biphenyl-3,5-dicarboxylate (MBPDC).

88. The MAMS of claim 78, wherein the metal clusters comprise at least one ion of metals selected from the group consisting of Al, Ge, and Ga.

89. The MAMS of claim 78, wherein the amphiphilic ligand is selected from the group consisting of:

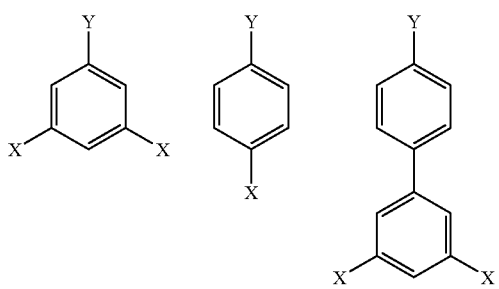

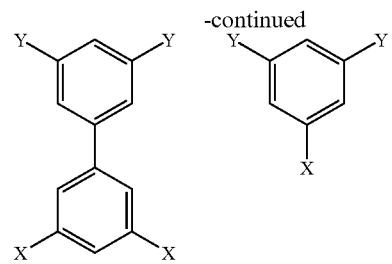

wherein:
X is at least one of carboxylate, cyano, phosphonate, sulfonate, imidazolate, pyridine, pyrazole, and tetrazolate; and
Y is at least one of tert-butyl, methyl, isopropyl, trifluoromethyl, butoxyl, butylsulfonyl, alkyl, halogenated alkyl, alkenyl, alkynyl, and alkoxyl.

90. The MAMS of claim 78, wherein the at least one hydrophilic pore reaches the structural limits of the MAMS.

91. The MAMS of claim 78, wherein at least one hydrophobic moiety substantially faces at least one other hydrophobic moiety in a spaced-apart relationship.

92. The MAMS of claim 78, wherein the at least one hydrophilic pore exhibits an atom-to-atom distance of about 8 Angstroms (Å).

93. The MAMS of claim 92, wherein the at least one hydrophilic pore exhibits an atom-to-atom distance of about 5 Å considering van der Waals radii.

94. The MAMS of claim 78, wherein the metal clusters are coordinatively bound with the functionalized hydrophilic moieties.

95. The MAMS of claim 78, wherein the plurality of tri-layers pack in a graphitic structure.

96. A method of separating gaseous molecules, comprising contacting the MAMS of claim 78 with a mixture of molecules selected from the group consisting of $H_2/N_2$, $H_2/CO$, $N_2/O_2$, $N_2/CH_4$, $CH_4/C_2H_4$ and $C_2H_4/C_3H_6$, wherein the molecules are separated from their respective pair.

97. A method of adsorbing a molecular species selected from the group consisting of $H_2$, $N_2$, $O_2$, CO, Ar, $CH_4$, $C_2H_4$, and $C_3H_6$, comprising contacting the MAMS of claim 78 with a mixture of molecular species comprising one of $H_2$, $N_2$, $O_2$, CO, Ar, $CH_4$, $C_2H_4$, and $C_3H_6$.

98. A metal-organic framework-based mesh-adjustable molecular sieve (MAMS), comprising:
a plurality of $Ni_8(\mu_3\text{-OH})$ clusters;
a plurality of 5-tert-butyl-1,3-benzenedicarboxylate ligands (5-BBDC), each ligand comprising:
a tert-butyl moiety; and
a dicarboxylate moiety; and
wherein:
a plurality of $Ni_8(\mu_3\text{-OH})_4$ clusters are bound with a plurality of dicarboxylate moieties to form a metal cluster layer, the metal cluster layer forming at least one hydrophilic pore, the hydrophilic pore exhibiting an atom-to-atom distance of about 8 Å and about 5 Å considering van der Waals radii;
at least one hydrophilic pore reaches the structural limits of the MAMS;
on each side of the metal cluster layer, a plurality of associated tert-butyl moieties cooperate with the metal cluster layer to form a tri-layer; and a plurality of tri-layers are packed in a facing, spaced-apart relationship to form at least one hydrophobic pore.

99. The MAMS of claim 98, wherein the MAMS exhibits a temperature-dependent mesh size.

100. The MAMS of claim 99, wherein the temperature-dependent mesh size varies between about 2.9 Å and about 5 Å.

101. The MAMS of claim 98, wherein the MAMS exhibits a temperature-dependent molecular gating effect.

102. The MAMS of claim 98, wherein:
the eight octa-nickel atoms are divided into four pairs by a two-fold axis through the center of the cluster; and
wherein:
a first Ni pair is bound to five carboxylate O atoms from four 5-BBDC ligands and one $\mu_3$-OH groups;
a second Ni pair is bound to three carboxylate O atoms and three $\mu_3$-OH groups;
a third Ni pair is bound to four carboxylate O atoms and one $\mu_3$-OH group; and
a fourth Ni pair is bound to two carboxylate O atoms and one $\mu_3$-OH group.

103. A method of adsorbing a molecular species selected from the group consisting of $H_2$, $N_2$, $O_2$, CO, Ar, $CH_4$, $C_2H_4$, and $C_3H_6$, comprising placing the MAMS of claim 98 into a mixture of molecular species comprising one of $H_2$, $N_2$, $O_2$, CO, Ar, $CH_4$, $C_2H_4$, and $C_3H_6$.

104. A metal-organic framework-based mesh-adjustable molecular sieve (MAMS).

105. The MAMS of claim 104, wherein the MAMS is selected from the group consisting of:
$Ni_8(\mu_3\text{-OH})_4(BBDC)_6$;
$Cu_2(MBPDC)_2$;
$Co_2(BBPDC)_2$;
$Mn_2(BBPDC)_2$;
$Zn_2(BBPDC)_2$;
$Cu_2(BBPDC)_2$; and
$Cu_XL_Y$;
wherein:
BBDC is 5-tert-butyl-1,3-benzenedicarboxylate;
MBPDC is 4'-methyl-biphenyl-3,5-dicarboxylate;
BBPDC is 4'-tert-butyl-biphenyl-3,5-dicarboxylate;
L is a suitable ligand; and
X and Y are determined by charge balance.

106. 4'-methyl-biphenyl-3,5-dicarboxylic acid ($H_2MBPDC$).

107. A method of synthesizing the compound of claim 106, comprising the steps of:

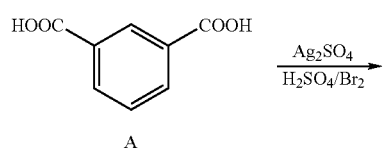

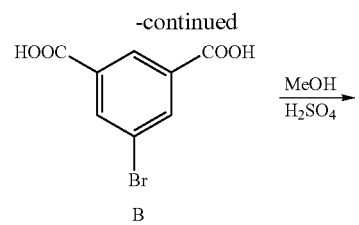

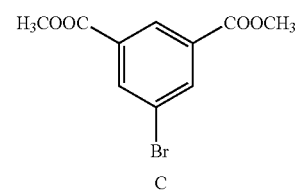

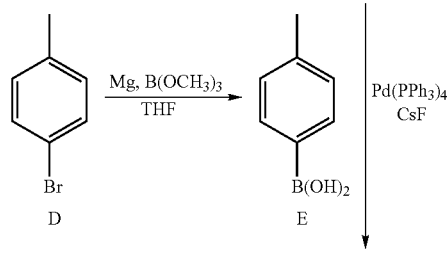

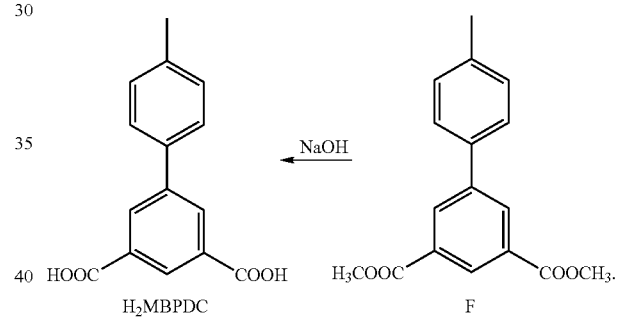

108. The dicarboxylate ion (MBPDC) of the acid of claim 106.

109. 4'-tert-butyl-biphenyl-3,5-dicarboxylic acid ($H_2BBPDC$).

110. A method of synthesizing the compound of claim 109, comprising the steps of:

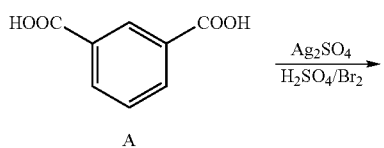

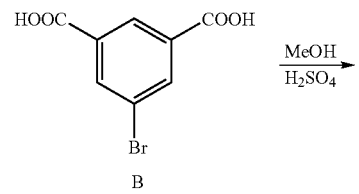

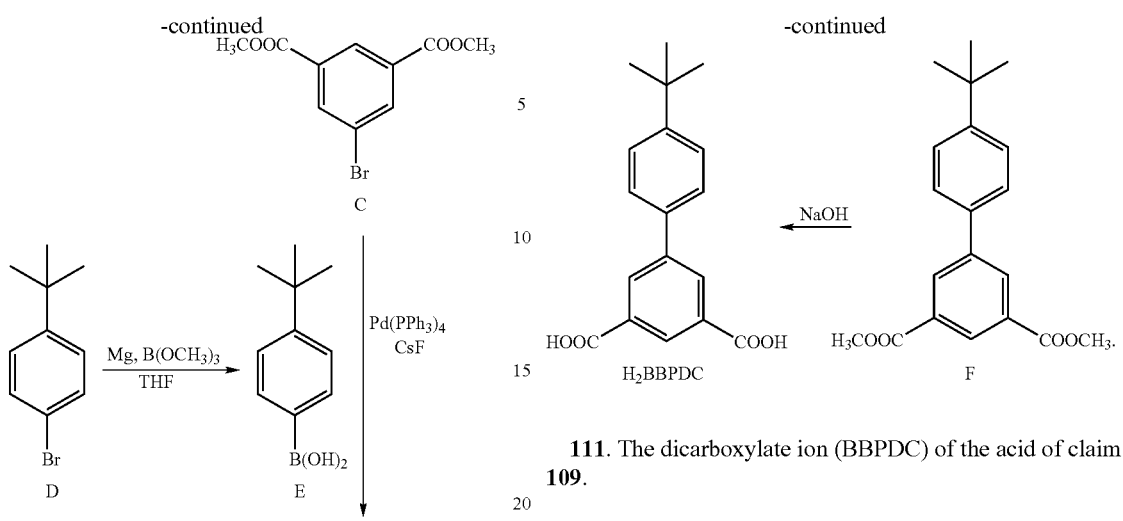
111. The dicarboxylate ion (BBPDC) of the acid of claim 109.
* * * * *

UNITED STATES PATENT AND TRADEMARK OFFICE
CERTIFICATE OF CORRECTION

PATENT NO. : 7,687,432 B2  Page 1 of 3
APPLICATION NO. : 11/738730
DATED : March 30, 2010
INVENTOR(S) : Zhou et al.

It is certified that error appears in the above-identified patent and that said Letters Patent is hereby corrected as shown below:

The sheets of drawings consisting of figures 2 and figure 9, should be deleted to appear as per attached figures 2 and 9.

Claim 21: column 10: lines 22-23: "adsporption temperature, T deg, K, is selected according to the equation" should be changed to: --adsorption temperature, T deg. K, is selected according to the equation--, and the claim read as follows:

21. The method of claim 20, wherein the adsorption temperature, T deg. K, is selected according to the equation D = 0.0076 T + 2.76, where D is the kinetic diameter, in Angstroms, of the molecular species of interest.

Claim 23: column 10: line 44: "The MAMS of claim 19, wherein the MAMS exhibits" should be changed to: --The MAMS of claim 22, wherein the MAMS exhibits--, and the claim read as follows:

23. The MAMS of claim 22, wherein the MAMS exhibits a temperature-dependent mesh size.

Claim 40: column 11: line 58: "A method of separating gaseous molecules, comprising" should be changed to: --A method of separating molecules, comprising--, and the claim read as follows:

40. A method of separating molecules, comprising contacting the MAMS of claim 22 with a mixture of molecules selected from the group consisting of H2/N2, H2/CO, N2/O2, N2/CH4, CH4/C2H4 and C2H4/C3H6, wherein the molecules are separated from their respective pair.

Signed and Sealed this

Twenty-first Day of December, 2010

David J. Kappos
*Director of the United States Patent and Trademark Office*